US008343458B2

(12) United States Patent  
Bogyo et al.

(10) Patent No.: US 8,343,458 B2  
(45) Date of Patent: Jan. 1, 2013

(54) PROBES FOR IN VIVO TARGETING OF ACTIVE CYSTEINE PROTEASES

(75) Inventors: Matthew S. Bogyo, Redwood City, CA (US); Galia Blum, Jerusalem (IL); Alicia Berger, San Francisco, CA (US); Zhen Cheng, Stanford, CA (US); Sanjiv S. Gambhir, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 532 days.

(21) Appl. No.: 12/418,116

(22) Filed: Apr. 3, 2009

(65) Prior Publication Data

US 2009/0252677 A1 Oct. 8, 2009

Related U.S. Application Data

(60) Provisional application No. 61/042,151, filed on Apr. 3, 2008.

(51) Int. Cl.
*A61K 51/00* (2006.01)
*A61M 36/14* (2006.01)

(52) U.S. Cl. ............... 424/1.69; 424/1.11; 424/1.65; 424/9.1; 424/9.3; 424/9.34; 424/9.4

(58) Field of Classification Search .............. 424/1.11, 424/1.65, 1.69, 1.81, 1.85, 1.89, 9.1, 9.2, 424/9.3, 9.4, 9.5, 9.6, 9.7, 9.8, 9.34; 514/1, 514/1.11, 20.1, 20.2; 534/7, 10–16; 530/300, 530/331, 332, 333, 334; 206/223, 569, 570
See application file for complete search history.

(56) References Cited

U.S. PATENT DOCUMENTS

| | | | |
|---|---|---|---|
| 5,424,186 A | 6/1995 | Fodor et al. | |
| 5,780,007 A | 7/1998 | Dean et al. | |
| 6,475,485 B1 | 11/2002 | Bandman et al. | |
| 6,531,474 B1 * | 3/2003 | Wannamaker et al. | 514/248 |
| 6,673,333 B1 | 1/2004 | Meade et al. | |
| 2002/0150961 A1 | 10/2002 | Bogyo et al. | |
| 2004/0131544 A1 | 7/2004 | MacLean et al. | |
| 2005/0002866 A1 | 1/2005 | Meade et al. | |
| 2006/0154325 A1 | 7/2006 | Bogyo et al. | |
| 2006/0275843 A1 | 12/2006 | Nepveu et al. | |
| 2007/0036725 A1 | 2/2007 | Bogyo et al. | |
| 2007/0141624 A1 | 6/2007 | Winn | |
| 2010/0003735 A1 | 1/2010 | Bogyo et al. | |
| 2010/0068150 A1 | 3/2010 | Bogyo et al. | |

OTHER PUBLICATIONS

Amir M. Sadaghiani, et al., "Tagging and detection strategies for activity-based proteomics," Current Opinion in Chemical Biology, Feb. 2007, vol. 11, 1-9.
Kati Mattila, et al., "Derivatization of phosphopeptides with mercapto- and amino-functionalized conjugate groups by phosphate elimination and subsequent Michael addition," Org. Biomol. Chem., 2005, vol. 3, 3039-3044.
Daisuke Kato, et al., "Activity-based probes that target diverse cysteine protease families," Nature Chemical Biology, Jun. 2005, vol. 1, No. 1, 33-38.
Galia Blum, et al., "Noninvasive optical imaging of cysteine protease activity using fluorescently quenched activity-based probes," Nature Chemical Biology, published online Sep. 9, 2007.
Katherine M. Bell-McQuinn, et al., Inhibition of Cysteine Cathepsin Protease Activity Enhances Chemotherapy Regimens by Decreasing Tumor Growth and Invasiveness in a Mouse Model of Multistage Cancer, Cancer Res, Aug. 2007, vol. 67, No. 15, 7378-7385.
Matthew P. Patricelli, "Activity-based probes for functional proteomics," Briefings in Functional Genomics and Proteomics, Jul. 2002, vol. 1, No. 2, 151-158.
Galia Blum, et al., "Dynamic imaging of protease activity with fluorescently quenched activity-based probes," Nature Chemical Biology, Aug. 14, 2005, vol. 1, No. 4, 203-209.
Marko Fonovic, et al., "Activity Based Probes for Proteases: Applications to Biomarker Discovery, Molecular Imaging and Drug Screening," Current Pharmaceutical Design, Feb. 2007, vol. 13, 253-261.
Fang Yuan, et al., "A Selective Activity-Based Probe for the Papain Family Cysteine Protease Dipeptidyl Peptidase I/Cathepsin C," J. Am. Chem. Soc., web release date Apr. 8, 2006, Abstract.
Weissleder, Ralph, et al., "In vivo imaging of tumors with protease-activated near-infrared fluorescent probes," Nature Biotechnology, Apr. 1999, vol. 17, 375-378.
Berger, Alicia B., et al., "Identification of Early Intermediates of Caspase Activation Using Selective Inhibitors and Activity-Based Probes," Molecular Cell, Aug. 18, 2006, 509-521.
Berger, Alicia B., et al., "Commonly used caspase inhibitors designed based on substrate specificity profiles lack selectivity," Cell Research advance online publication, Nov. 21, 2006, 1-3.
Sexton, Kelly B., et al., "Design of cell-permeable, fluorescent activity-based probes for the lysosomal cysteine protease asparaginyl endopeptidase (AEP)/legumain," Bioorganic & Medicinal Chemistry Letters, Nov. 2006, 17, 649-653.
Roy, Sophie, et al., Maintenance of caspase-3 proenzyme dormancy by an intrinsic "safety catch" regulatory tripeptide, PNAS, May 22, 2001, vol. 98, No. 11, 6132-6137.
Thornberry, Nancy A., et al., "Inactivation of Interleukin-1Beta Converting Enzyme by Peptide (Acyloxy)methyl." Biochemistry, 1994, 33, 3934-3940, (only p. 3934 was submitted).
Choe, Youngchool, et al., "Substrate Profiling of Cysteine Proteases Using a Combinatorial Peptide Library Identifies Functionally Unique Specificities," J. Biol. Chem., May 5, 2006, vol. 281, No. 18, 12824-12832.
Bogyo, Matthew, et al., "Substrate binding and sequence preference of the proteasome revealed by active-site directed affinity probes," Research Paper, Chemistry & Biology, Jun. 1998, 5:307-320.
PCT/US09/39496 International Search Report and Written Opinion, Jun. 11, 2009.

* cited by examiner

*Primary Examiner* — D L Jones
(74) *Attorney, Agent, or Firm* — David J. Aston; Peters Verny, LLP

(57) ABSTRACT

Activity-based probes, which are specific for certain active cysteine proteases (caspase, cathepsin and legumain) and carry radioactive labels, are disclosed. The present probes comprise an acyloxymethyketone (AOMK) "warhead" that binds only to active enzyme. The probes further comprise peptide-like structure that targets the probe to a specific cysteine protease or protease family, and a radiolabel on the probe, which is bound to the targeted enzyme. It has been found that the present probes are stable in vivo and give specific target images distinguishable over background. The preferred probes are labeled with a positron-emitting agent such as $^{64}$Cu, $^{125}$I (SPECT) and $^{99m}$Tc (PET). The probes show in vivo half-life and stability well suited for imaging.

29 Claims, 15 Drawing Sheets

1A
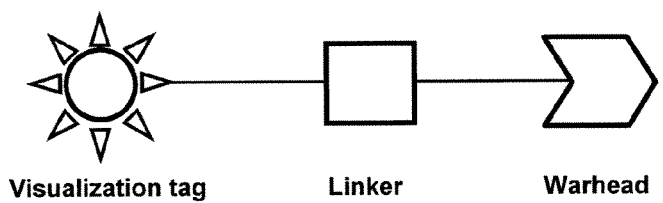
1B
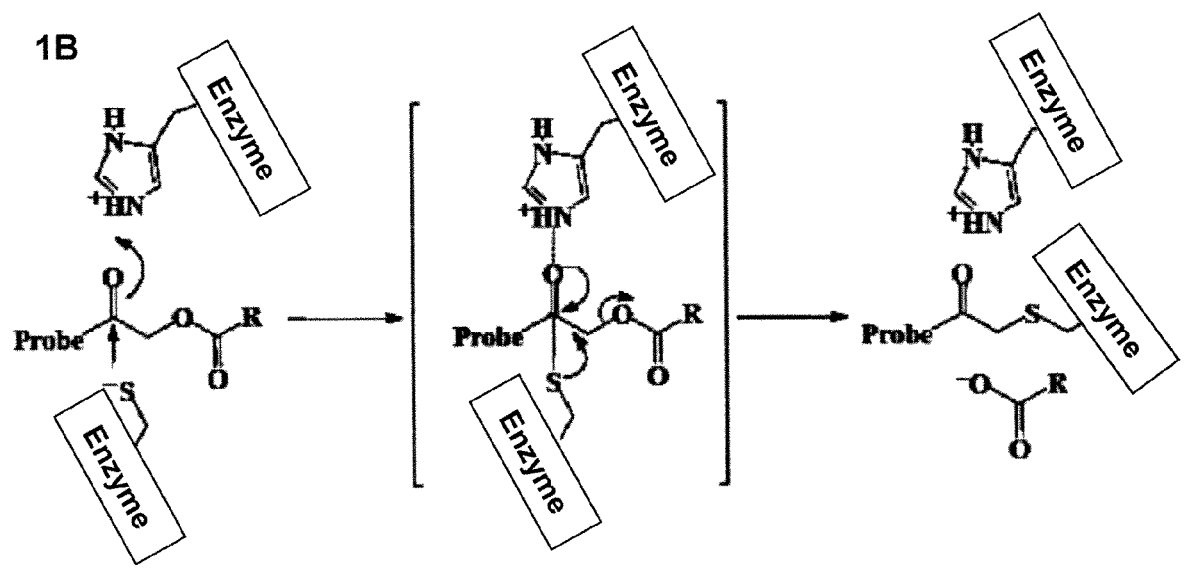
Figure 1A-B

2B
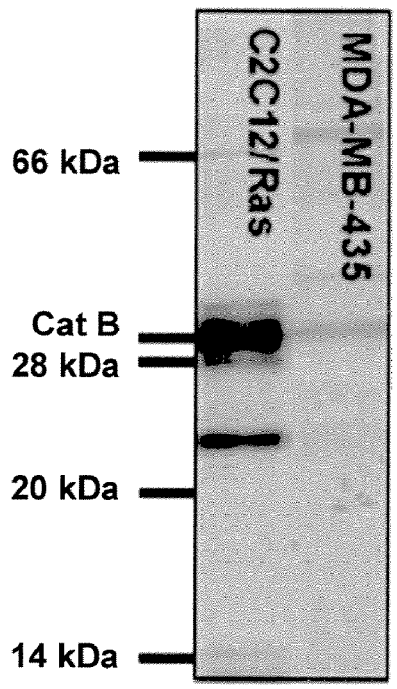
2C
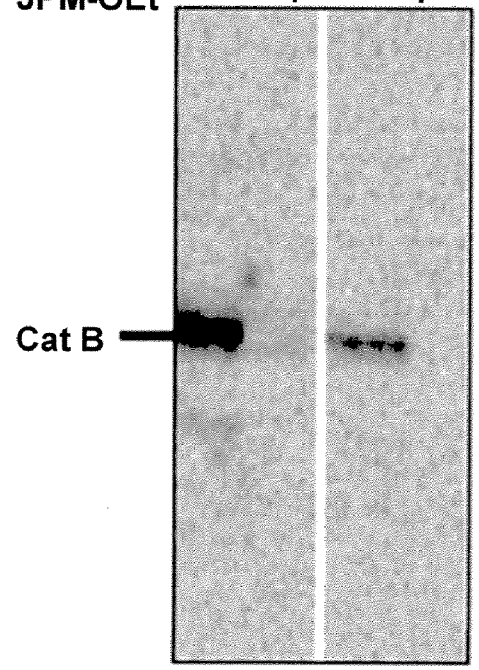
Figure 2B-C

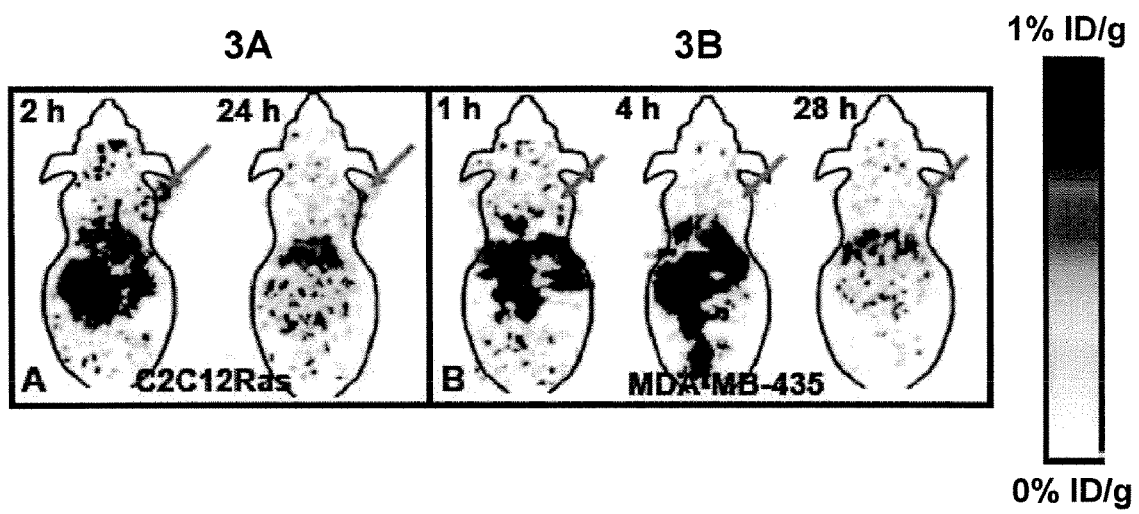
Figure 3A-B

| cmpd # | Amino Acid | Structure |
|---|---|---|
| 1 | (2furyl)alanine | 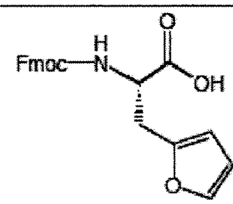 |
| 2 | (2thienyl)alanine | 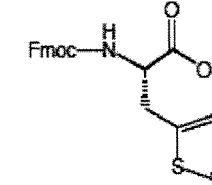 |
| 3 | 2pyridylAla | 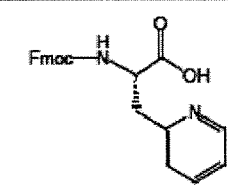 |
| 4 | 1amino1cyclohexane carboxylic acid | 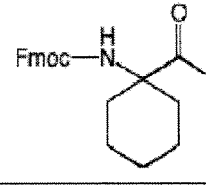 |
| 5 | 1amino1cyclopentanecarboxylic acid | 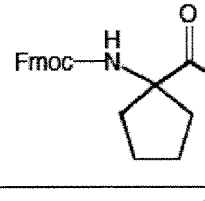 |
| 6 | 2-Abz | 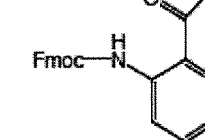 |
| 7 | 3Abz | 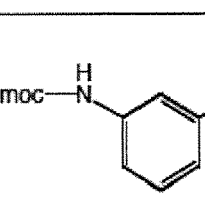 |
Figure 4

| # | Name | Structure |
|---|---|---|
| 8 | 2Abu | Fmoc-NH-CH(CH2CH3)-COOH |
| 9 | 3amino3phenylpropionic acid | Fmoc-NH-CH(Ph)-CH2-COOH |
| 10 | dehydroAbu | Fmoc-NH-C(=CHCH3)-COOH |
| 11 | ACPC | Fmoc-NH-C(cyclopropyl)-COOH |
| 12 | Aib | Fmoc-NH-C(CH3)2-COOH |
| 13 | AllylGly | Fmoc-NH-CH(CH2CH=CH2)-COOH |
| 14 | Amb | Fmoc-NH-CH2-(C6H4)-COOH |
| 15 | Amc | Fmoc-NH-CH2-(cyclohexyl)-COOH |

Figure 4 (cont.)

| 16 | Bip | 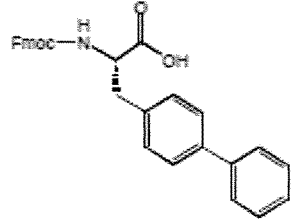 |
| 17 | Bpa | 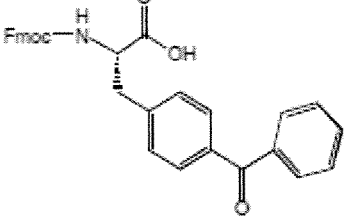 |
| 18 | Cba | 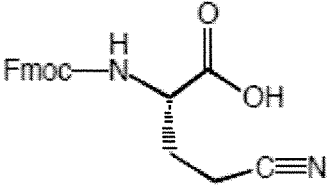 |
| 19 | Cha | 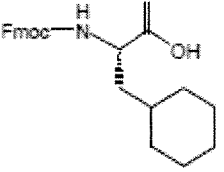 |
| 20 | deltaLeu | 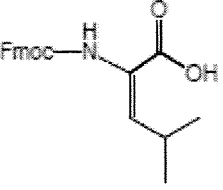 |
| 21 | deltaVal | 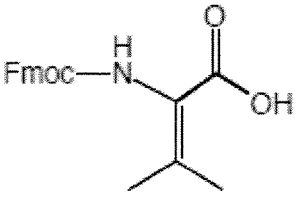 |
| 22 | Hyp | 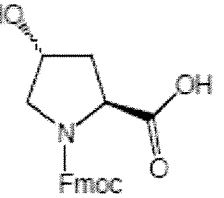 |
Figure 4 (cont.)

| 23 | Igl | |
| 24 | Inp | |
| 25 | 1-Nal | |
| 26 | 2-Nal | |
| 27 | Nva | |
| 28 | 4-nitroPhe | |
| 29 | 4MethylPhe | |

Figure 4 (cont.)

| | | | |
|---|---|---|---|
| 30 | | 4Methyl-DPhe | Fmoc-NH-CH(CH2-C6H4-CH3)-COOH structure |
| 31 | | Phe(pI) | Fmoc-NH-CH(CH2-C6H4-I)-COOH structure |
| 32 | | Phe4NH(Boc) | Fmoc-NH-CH(CH2-C6H4-NH-Boc)-COOH structure |
| 33 | | hPhe | Fmoc-NH-CH(CH2CH2-C6H5)-COOH structure |
| 34 | | Phg | Fmoc-NH-CH(C6H5)-COOH structure |
| 35 | | pip | Fmoc-piperidine-2-carboxylic acid structure |
| 36 | | Dpip | Fmoc-D-piperidine-2-carboxylic acid structure |

Figure 4 (cont.)

| 37 | propargylglycine | 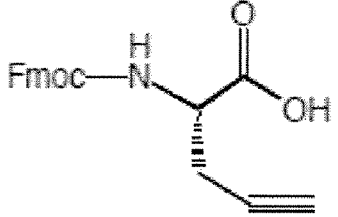 |
| 38 | Thz | 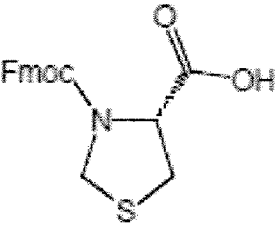 |
| 39 | Tic | 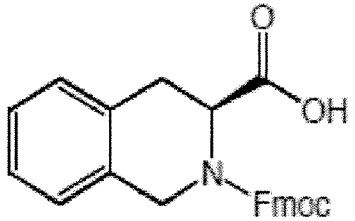 |
| 40 | Tle | 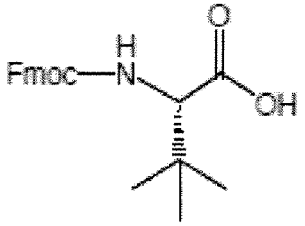 |
| 41 | 3-NitroTyr | 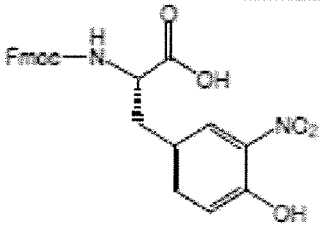 |
| 42 | leu | 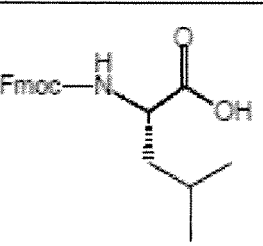 |
Figure 4 (cont.)

PROBES FOR IN VIVO TARGETING OF ACTIVE CYSTEINE PROTEASES

CROSS-REFERENCE TO RELATED APPLICATIONS

This application claims priority from U.S. Provisional Patent Application No. 61/042,151, filed on Apr. 3, 2008, which is hereby incorporated by reference in its entirety.

STATEMENT OF GOVERNMENTAL SUPPORT

This invention was made with Government support under contracts RR020843, EB005011, and CA114747 awarded by the National Institutes of Health. The Government has certain rights in this invention.

REFERENCE TO SEQUENCE LISTING, COMPUTER PROGRAM, OR Compact Disk

None

BACKGROUND OF THE INVENTION

1. Field of the Invention

The present invention relates to the field of labeled activity-based probes which bind to active cysteine proteases, including cathepsins and caspases, and the use of such probes as radioactive imaging agents in vivo.

2. Related Art

Proteases play important roles in the regulation of both normal and disease processes. The cysteine protease family comprises six major families: the papain family, calpains, clostri-pains, streptococcal cysteine proteases, viral cysteine proteases and most recently established, caspases (also called apopains). In particular the papain family cysteine cathepsins are frequently over-expressed at the mRNA, protein and activity levels in a number of human cancers such as glioma, melanoma, breast, colorectal, gastric, lung, and prostate carcinomas. In addition, expression of a number of cysteine cathepsins, including cathepsin B and L, is increased in pre-neoplastic lesions and changes in both localization and subcellular distribution of these proteases are often observed in tumors. This combination of increased expression, activity and altered localization of these enzymes as well as their positive association with tumor progression, metastatic potential and disease outcome make them potentially valuable cancer biomarkers. The cathepsin family of lysosomal protease includes the cysteine proteases; cathepsins B, H, K, L, W, C, F, V, X, and S, and the aspartyl protease; cathepsins D, and the serine protease cathepsin G. The various members of this endosomal protease family are differentially expressed. Some, such as cathepsin D, have a ubiquitous tissue distribution, while others, such as cathepsin S, are found mainly in monocytes, macrophages, and other cells of the immune system. The activity of cysteine proteinases is optimal at pH values of <7, as found in lysosomes, where these enzymes perform their main biological function. However, there is increasing evidence for extracellular functions of cathepsins produced by macrophages, osteoclasts, fibroblasts, and transformed cells into specific pericellular locations and that these proteases can function well in neutral pH environments as well, (See, Oksjoki et al., "Differential expression patterns of cathepsins B, H, K, L and S in the mouse ovary," Molecular Human Reproduction, Vol. 7, No. 1, 27-34, January 2001.)

In addition, the present imaging and labeling agents may be directed against caspases. Initiator caspases (e.g., CASP2, CASP8, CASP9 and CASP10) cleave inactive pro-forms of effector caspases, thereby activating them. Effector caspases (e.g., CASP3, CASP6, CASP7) in turn cleave other protein substrates within the cell resulting in the apoptotic process. Such probes can be useful in imaging active apoptotic processes in a cell.

Molecular imaging is a valuable new technology that is helping to provide a better understanding of cancer and other diseases. Novel imaging methods and molecularly targeted tracers can now be used to not only to locate a tumor, but also to visualize the expression and activity of specific molecular targets and biological processes in a tumor. These imaging methods have the potential to facilitate both early disease detection and to aid in the process of drug development. Directed targeting of enzymatic proteins such as protease using imaging agents has the potential to provide even more detail about the basic biological framework of a tumor and also provide better resolution of the disease phenotype. In addition since most proteases are initially synthesized as inactive zymogens that are activated by a complex set of post-translational mechanisms, tools that report on enzyme activity and not simple protein abundance will be required to fully understand their function in complex biological processes. For this reason, a number of recent studies have focused on the development of protease directed imaging agents that act as substrates for a target enzyme. This approach takes advantage of the catalytic nature of the target in order to amplify a signal from a reporter substrate. Strategies that make use of quenched fluorescent substrates and also fluorescent molecules that only penetrate a cellular membrane when processed by a target protease have been developed. While all of these methods have provided valuable new tools for the optical imaging of protease activity in vivo, none of these methods have been translated for use in radiological imaging.

Described and exemplified below is the development and application of radiolabeled small molecule activity based probes that can be used for positron emission tomography (PET) imaging of cysteine cathepsin and caspase activity. These probes have a reactive group as in the peptide acyloxymethyl ketone (AOMK) probes that have been reported to be highly selective labels of a number of classes of cysteine cathepsins. This class of activity-based probes has also recently been used for optical imaging of cysteine cathepsin activity in live cells (Blum et al. Nat Chem Bio 2005, below) and in near-infrared (NIRF) labeled form for non-invasive optical imaging of cysteine cathepsin activity in living subjects. The present, novel probes couple the intrinsic advantages of nuclear imaging including high sensitivity, capability of quantification, and clinical translation with the specific, covalent nature of these small molecule imaging agents. In addition, their relatively small size compared to substrate based probes gives them favorable in vivo pharmacodynamic properties and cellular uptake. In examples below, it is shown that a $^{64}$Cu-labeled derivative of the previously reported cysteine cathepsin probe GB111 (disclosed in U.S. patent application Ser. No. 11/502,255 filed Aug. 10, 2006) is taken up by tumors and provides good signal to background ratios. Furthermore, the relative levels of probe labeling in tumors directly correlates with the activity levels of cathepsins B and L in those tumors as demonstrated by biochemical profiling methods. Thus, these new probes represent potentially valuable imaging tools for application to a number of clinically relevant diseases that involve overexpression of cysteine cathepsin activity.

Specific Patents and Publications

Kato D, Boatright K M, Berger A B, Nazif T, Blum G, Ryan C, Chehade K A, Salvesen G S, Bogyo M, "Activity-based probes that target diverse cysteine protease families," *Nat Chem Biol*, 2005; 1: 33-8, describes a series of quenched near-infrared fluorescent activity-based probes (qNIRF-ABPs) that covalently target the papain-family cysteine proteases shown previously to be important in multiple stages of tumorigenesis. These 'smart' probes emit a fluorescent signal only after covalently modifying a specific protease target. This paper discloses the compound Z-FR-AOMK shown in FIG. 1 of the present application. The Z-FR-AOMK was active only against cathepsin B, not cathepsins Z, H, J, H or C. It also gives a detailed synthetic method, which may be adapted according to the teachings below to make compounds of the present invention.

Weissleder et al., "In vivo imaging of tumors with protease-activated near-infrared fluorescent probes," *Nature Biotechnology*, 17, 375-378 (1999) describe the imaging of tumor-associated lysosomal protease activity using autoquenched near-infrared fluorescence (NIRF) probes. The authors used a synthetic graft copolymer consisting of poly-L-lysine sterically protected by multiple methoxypolyethylene glycol (MPEG) side chains.

Blum et al., "Noninvasive optical imaging of cysteine protease activity using fluorescently quenched activity-based probes," *Nature Chemical Biology*, 3, 668-677 (2007) disclose a series of quenched near-infrared fluorescent activity-based probes (qNIRF-ABPs) that covalently target the papain-family cysteine proteases shown previously to be important in multiple stages of tumorigenesis. These 'smart' probes emit a fluorescent signal only after covalently modifying a specific protease target. As a starting point, the authors (which include present inventors) used the peptide acyloxymethylketones (AOMKs) GB111 and GB117 that were recently described as tools for cell-based imaging of cysteine cathepsin activity (see paper cited below).

Blum, G. et al. Dynamic imaging of protease activity with fluorescently quenched activity-based probes. *Nat. Chem. Biol.*, 1, 203-209 (2005), discloses the acyloxymethyl ketone (AOMK) reactive group for probe design, as this 'warhead' targets diverse families of cysteine proteases. More importantly, the mechanism of covalent modification of a cysteine probes based on the acyloxymethyl ketone (AOMK) reactive group for probe design, which targets diverse families of cysteine proteases. Those probes target the papain family of cysteine proteases, as this family has been extensively studied with ABPs and a number of cell-permeable reagents have successfully been designed. The authors (which include present co-inventors) carried out the synthesis of the resulting quenched probe GB117 and its corresponding nonquenched control GB111 using a combination of solid and solution-phase chemistries.

U.S. Pat. No. 6,475,485 discloses two novel human cathepsin proteins, referred to as HCP-1 and HCP-2 and, collectively, HCPs, which share features with other proteins involved in proteolysis.

Joyce et al., "Cathepsin cysteine proteases are effectors of invasive growth and angiogenesis during multistage tumorigenesis," *Cancer Cell, Vol* 5, 443-453, May 2004, disclose a broad-spectrum cysteine cathepsin inhibitor which was used to pharmacologically knock out cathepsin function at different stages of tumorigenesis, impairing angiogenic switching in progenitor lesions, as well as tumor growth, vascularity, and invasiveness.

BRIEF SUMMARY OF THE INVENTION

The following brief summary is not intended to include all features and aspects of the present invention, nor does it imply that the invention must include all features and aspects discussed in this summary.

The present invention comprises a composition useful for in vivo imaging of tissues having an active cysteine protease, comprising a compound according to the formula:

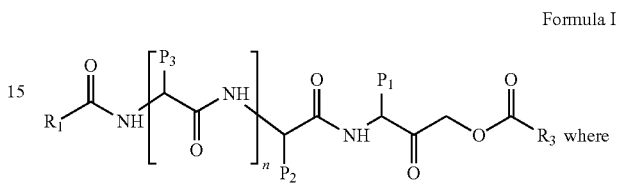

Formula I n is an integer between 0 and 2, $P_3$ being absent when n=0, and there being a $P_4$ only when n=2;

$R_1$ and $R_3$ are independently selected from the groups consisting of H, $NH_2$, aminocarbonyl, aryl, substituted aryl (including 2-nitro, 3-hydroxy benzyl and N-benzyloxycarbonyl [cbz]), amino, lower alkyl, or cycloalkyl;

$P_1$, $P_2$, $P_3$ and $P_4$ are independently amino acid side chains selected from naturally occurring amino acid side chains and those listed in FIG. 4; and one of $R_1$, $R_3$ or a $P_1$, $P2_2$, $P_3$ or $P_4$ further is bonded to a chelator or a radiolabel.

Formula I contains $R_1$ and $R_3$ capping groups which may be an optionally substituted benzyl, as illustrated, for example in FIGS. 1 and 2A. That is, the benzyl may have additional substituents such as methyl or nitro groups, and it may be linked to an oxygen or other heteroatom a carbonyl carbon, etc.

The compositions according to the present invention will have a structure so as to include a radiolabel, preferably attached by a chelator, such as DOTA or its derivatives. $R_1$ or $P_1$ may further comprise the chelator. In one preferred embodiment, the chelator is on $P_1$, and where $P_1$ contains 2-5 carbon atoms (see, e.g., FIG. 2).

As shown in FIG. 2, the chelator 10, in one embodiment, is linked by an amide linkage to a lower alkyl group in $P_1$. $P_2$, $P_3$ or $P_4$ may also be so structured.

In certain aspects of the present invention, the chelator is selected from the group consisting of: diethylenetriaminepentaacetic acid (DTPA), ethylenediaminetetraacetic acid (EDTA), 1,4,7,10-tetraazacyclododecane-N,N',N'',N'''-tetraacetate (DOTA), tetraazacyclotetradecane-N,N',N'',N'''-tetraacetic acid (TETA), hydroxyethylidene diphosphonate (HEDP), dimercaptosuccinic acid (DMSA), diethylenetriaminetetramethylenephosphonic acid (DTTP) and 1-(p-aminobenzyl)-DTPA, 1,6-diamino hexane-N,N,N',N'-tetraacetic acid, DPDP, and ethylenebis (oxyethylenenitrilo)-tetraacetic acid.

In certain aspects, the present invention concerns the in vivo administration of an active cysteine protease probe linked to a positron emitter, wherein the emitter is useful in PET, which is here intended to include related techniques such as SPECT. The radiolabel is advantageously selected from the group consisting of: $^{131}I$, $^{99m}TC$, $^{111}In$, $^{18}F$, $^{64}Cu$, $^{76}Br$, $^{86}Y$, $^{55}Co$ and $^{124}I$ and $^{125}I$.

The present compositions contemplate a variety of specific embodiments according to the definition of Formula I. $P_1$, which is adjacent to the AOMK, may be an acidic side chain such as D, or it may be basic such as R. $P_2$ is P or aryl, depending on the specificity to a particular protease that is desired. Likewise, $P_3$ may be aryl. Bulky side chains here tend to favor caspase binding. $P_2$, $P_3$ and $P_4$ may be as defined in Table I for a compound listed there, e.g., in AB28.

In one aspect, the present invention may comprise the use of end groups at $R_1$ and $R_3$, which are aryl and may serve as hydrophobic and protecting groups.

The present compositions and methods are directed to particular members of the cysteine protease family, depending on the condition being studied. These members are cathepsins, caspases and legumain. Further, specific cathepsins may be selected, as well as specific members of the caspase family.

Since radionuclides are involved, the present compositions may be embodied in a kit, adapted for use with a radiolabel that will be prepared shortly before administration of the probe.

In the present imaging methods, the composition is formulated in a pharmacologically acceptable carrier, with a radiolabel. The labeled compound is administered to the subject. After allowing the compound to circulate and enter the tissue, one obtains an image of the administered compound after a time sufficient to allow the compound to bind to and be cleaved by active cysteine cathepsin, using a specialized camera, such as a PET camera with gamma detectors. The present compounds are physiologically tolerated and have sufficient half-life and tissue permeability, with stable labeling that portions of the subject that have higher levels of active cysteine protease can be distinguished from other portions. The various compounds according to Formulas I-IV may be used in these methods.

In certain other aspects, the present invention includes the attachment of a radiolabel to a cysteine protease specific AOMK compound containing 1-3 amino acid-like residues ($P_1$-$P_3$) through a macrocyclic chelator, such as DOTA. The macrocyclic chelator is reacted with a sulfonosuccimimide in order to couple it to the compound. Furthermore, one may also carry out the step of heating the compound in the presence of a radioactive metal to bind the radioactive metal to the macrocyclic chelator, which is DOTA, or substituted DOTA, as shown in U.S. Pat. No. 6,673,333 to Meade, et al., issued Jan. 6, 2004, entitled "Functional MRI agents for cancer imaging."

BRIEF DESCRIPTION OF THE DRAWINGS

FIG. 1 is a series of figures, which taken together, show the present mechanism and structures. FIG. 1A shows the general structure of an activity-based probe. FIG. 1B shows a mechanism of covalent inhibition of a cysteine protease by an acyloxymethyl ketone showing cleavage of the inhibitor and release of the —O—C(=O)—R fragment.

FIG. 2 is a series of figures which, taken together, show the structure and function of representative in vivo probes. FIGS. 2B and 2C are gels showing expression and activity of enzyme targets of such probe, with a radionuclide label attached to the illustrated structure, showing the expression and activity of CB in a mouse myoblast cell line C2C12Ras and human breast cancer cell line MDA-MB-435. FIGS. 2B and 2C shows labeling of cathepsin target in C2C12/Ras and MDA-MB-435 cells. Cells were pretreated with JPM-OEt (50 μM) (+) or with control DMSO (0.1%) (−) for 2 h and labeled by addition of $^{64}$Cu-Z-FK(DOTA)-AOMK (555 KBq, 15 μCi) to culture medium for 2 h. Cells were collected, lysed and analyzed after SDS-PAGE. The labeled proteases were visualized by scanning of the gel with a Typhoon 9410 imager.

FIG. 3 is a composite photograph showing mouse uptake of labeled probe, i.e., a series of photographs of imaged mice. For purposes of reproduction, the image is converted to black and white and reversed. Lightest to darkest is a range between 0% ID (injected dose)/g and 1% ID/g. FIG. 3A shows coronal microPET images of a athymic nude mouse bearing C2C12/Ras tumor at 2 hr (left) and 24 hr (right) after tail veil injection of (5.55 MBq, 150 μCi) $^{64}$Cu-Z-FK(DOTA)-AOMK. The location of the tumor shows good contrast to background and is indicated by arrows. FIG. 3B shows three images of coronal microPET images of a nude mouse bearing MDA-MB-435 breast cancer at 1, 4 and 28 hr after administration of (3.7 MBq, 100 μCi) $^{64}$Cu-Z-FK(DOTA)-AOMK. Arrows indicate location of tumors. The C2C12 Ras tumor shows more signal, due to higher expression of cathepsins.

FIG. 4 shows structural representations of different artificial amino acid side chains as embodiments of $P_1$, $P_2$, and, if present, $P_3$ and $P_4$.

DETAILED DESCRIPTION OF THE PREFERRED EMBODIMENT

Definitions

Figure 1C:
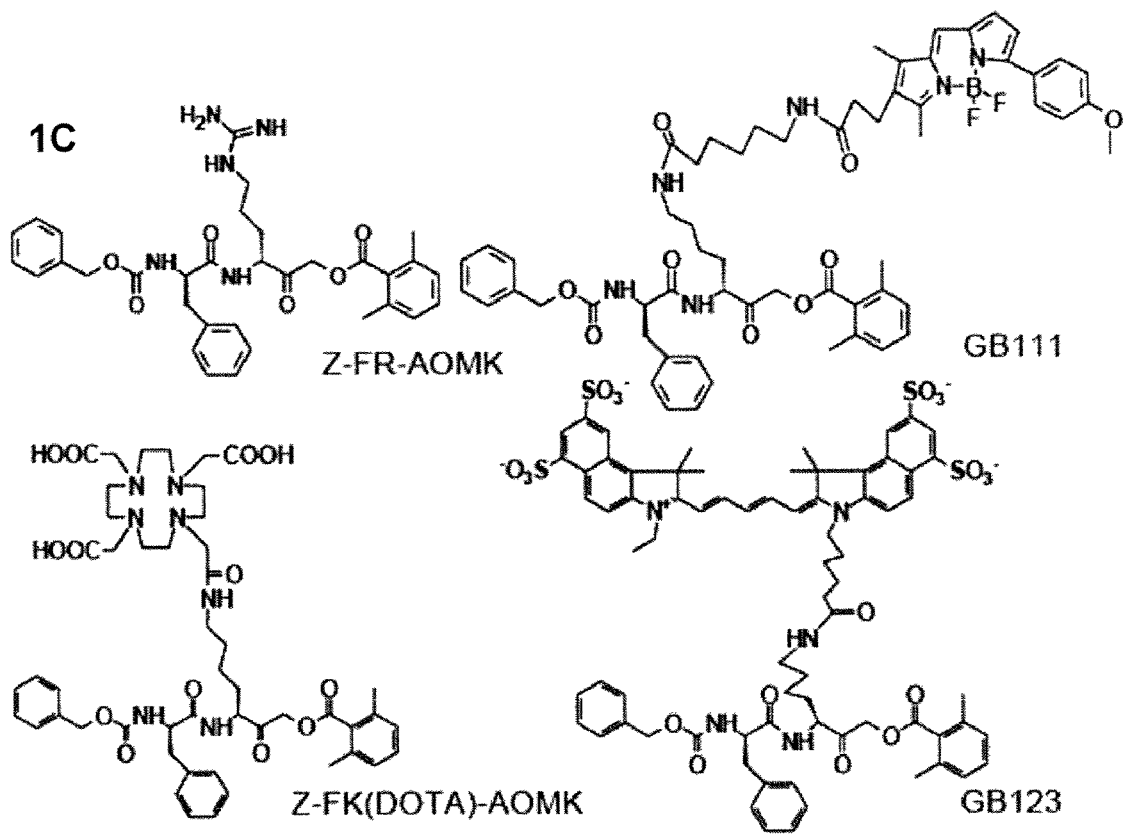
FIG. 1C shows a schematic representation of the molecular structure of Z-FR-AOMK, GB111, Z-FR-AOMK, and GB123.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "alkyl", alone or in combination with other groups, means a branched or straight-chain monovalent saturated aliphatic hydrocarbon radical of one to twenty carbon atoms, preferably one to sixteen carbon atoms, more preferably one to ten carbon atoms. The term "lower alkyl", alone or in combination with other groups, refers to a branched or straight-chain monovalent alkyl radical of one to ten carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like. Preferable lower alkyl residues are methyl ethyl and propyl, with methyl being especially preferred as a substituent on an aryl and propyl being preferred in a $P_1$-$P_4$ position. The term lower alkyl includes substituted alkyl, such as "perfluoro-lower alkyl", which refers to a lower alkyl group wherein all of the hydrogens of the lower alkyl group are substituted or replaced by fluoro. Among the preferred perfluoro-lower alkyl groups are trifluoromethyl, pentafluoroethyl and heptafluoropropyl, with trifluoromethyl being especially preferred. Also included are "alkoxy", which the group R'—O—, wherein R' is alkyl. The term "lower-alkoxy" refers to the group R"—O—, wherein R" is lower-alkyl. Examples of lower alkoxy groups are e.g., methoxy, ethoxy, propoxy, isopropoxy, butoxy, isobutoxy and hexyloxy, with methoxy being especially preferred. Also included is "lower alkylthio", which refers to the group R'—S—, wherein R' is lower-alkyl as defined above. The term "cycloalkyl" means a saturated ring containing 3 to 7 carbon atoms. Examples of said cycloalkyl include cyclopropyl, cyclohexyl and cycloheptyl.

The term "aryl" means an aromatic monovalent mono- or polycarbocyclic radical, such as phenyl diphenyl and naphthyl, preferably phenyl. Substituted aryl is aryl that is mono-, di- or tri-substituted, independently, by lower alkyl, lower alkoxy, halogen, amino or perfluoro-lower alkyl, preferably by lower alkyl, lower alkoxy and halogen. Especially preferred aryl groups include cbz (Z=—C—O— and Y=H in Formula IV), nitrophenol (Y=$O_2$N— and HO—), dimethyl benzyl (for $R_1$ and $R_3$) and phenyl, (e.g., Phe, Tyr) di-phenyl, and fused phenyl groups, such as Trp for $P_1$-$P_4$. Further examples of aryl groups include residues from FIG. 4 such as 16, 17, 19, 26 and 39. By way of example, an aryl group may be linked to a peptidyl analog by an alkylene group, as defined below.

The term "optionally substituted benzyl" means benzyl or benzyl which is substituted in the 2-, 3-, 4-, 5- and/or 6-position with lower alkyl or lower alkoxy, such as, for example, 4-methylbenzyl, 4-methoxybenzyl, 3-methylbenzyl and the like.

The term "alkylene" means erein, by itself or as part of another group, refers to straight and branched chain radicals of up to 10 carbons, unless the chain length is limited thereto. Typical examples include methylene (—$CH_2$—), ethylene (—$CH_2$ $CH_2$—), n-propylene (—$CH_2$ $CH_2$ $CH_2$—), isopropylene (—CH($CH_3$)$CH_2$— and —$CH_2$ CH($CH_3$)—), n-butylene (—$CH_2$ $CH_2$ $CH_2$ $CH_2$—), isobutylene, 3-methylpentylene (—$CH_2CH_2$ CH($CH_3$)$CH_2$ $CH_2$—), hexylene, heptylene, octylene, nonylene, and decylene.

The term "aminocarbonyl" means an amide group of the formula —C(=O)NH2.

The term "chelator," as used herein, by itself or as part of another group, means a chemical moiety that binds noncovalently to, or complexes with, one or more ions. Chelators can bind to lithium, calcium, sodium, magnesium, potassium, and/or other biologically important metal ions, although in the present case it binds too a radionuclide. The binding of the chelator to an ion can be determined by measuring the dissociation constant between a chelator and an ion. According to the invention, the dissociation constant $K_D$ between the chelator and the ion is from about $10^{-3}$ to about $10^{-15\ M.-1}$. Preferably, the dissociation constant $K_D$ between the chelator and the ion is from about $10^{-6}$ to about $10\text{-}15^{M.-1}$.

Examples of chelators are well known in the art. Preferably, the chelator binds a metal cation. Suitable chelators are bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate; dithiocarbamates; carboxylates; alkyldiamines; ethylenediamine (en); diethylenetriamine (dien); nitrate; nitro; nitroso; $(C_6H_5)_2$ $PCH_2$ $CH_2$ $P(C_6H_5)_2$ (diphos); glyme; diglyme; bis(acetylacetonate) ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTAi), 1,4,8,11-tetraazacyclotetradecanetetraacetic acid (TETA), DOTA-N-(2-aminoethyl) amide; DOTA-N-(2-aminophenethyl) amide; and 1,4,8,11-tetraazacyclotetradecane.

The present compounds may be made through the use of solid phase peptide synthesis techniques, which will employ known protective groups, capping groups, and the like. The term "capping group" refers to group has the effect of preventing further chemical reactions from occurring at that site, and is a non-amino acid moiety bonded to the C- or N-terminal of the peptide chain. Examples of common N-terminal capping groups used in peptide synthesis are Boc (t-butoxycarbonyl,) and Cbz (benzyloxycarbonyl). Other capping groups useful in synthesis are acetyl and adamantyl, dimethyl benzyl succinimidyl, 4-methylbenzyl, 2-thiophenylmethyl, 4-thiazolylmethyl, 3,5-difluorobenzyl, etc. Preferred capping groups for use as $R_1$ are carboxybenzyl and dimethyl benzoic acid. However, the capping group is variable.

The term "radiolabel" means a radioactive or paramagnetic substance attached to the probe either directly or through a chelator, and attached in sufficient quantity and activity to generate a signal in an organism, including a human. That is, the radiolabel forms part of the chemical structure of the inhibitor and is a radioactive or non-radioactive isotope present at a level significantly above the natural abundance level of said isotope. Such elevated or enriched levels of isotope are suitably at least 5 times, preferably at least 50 times the natural abundance level of the isotope in question, or present at a level where the level of enrichment of the isotope in question is 90 to 100% of the total quantity of radiolabel attached. Radiolabels may include $CH_3$ groups on the present probes with elevated levels of $^{13}C$ or $^{11}C$ and fluoroalkyl groups with elevated levels of $^{18}F$, such that the radiolabel is the isotopically labeled $^{13}C$, $^{11}1C$ or $^{18}F$ within the chemical structure of the probe. Preferred radiolabels are those which can be detected externally in a non-invasive manner following administration in vivo. The radiolabel is preferably chosen from: (i) a radioactive metal ion; (ii) a paramagnetic metal ion; (iii) a gamma-emitting radioactive halogen; (iv) a positron-emitting radioactive non-metal; and (v) a hyperpolarised NMR-active nucleus.

Most preferred radiolabels are radioactive, especially radioactive metal ions, gamma-emitting radioactive halogens and positron-emitting radioactive non-metals, particularly those suitable for imaging using SPECT or PET. These labels include radioactive transition elements plus lanthanides and actinides, and metallic main group elements. The semi-metals arsenic, selenium and tellurium are excluded from the scope. Suitable radiometals can be either positron emitters such as $^{64}Cu$, $^{48}V$, $^{52}Fe$, $^{55}Co$, $^{94m}Tc$ or $^{68}Ga$; or γ-emitters such as $^{99m}Tc$, $^{111}In$, $^{113m}In$, $^{67}Cu$ or $^{67}Ga$. Preferred radiometals are $^{99m}$Tc, $^{64}$Cu, $^{68}$Ga and $^{111}$In. Most preferred radiometals are γ-emitters, especially $^{99m}$Tc, which is the most preferred radionuclide for SPECT imaging.

When the radiolabel is a paramagnetic metal ion, suitable such metal ions include: Gd (III), Mn (II), Cu (II), Cr (III), Fe (III), Co (II), Er (II), Ni (II), Eu (III) or Dy (III). Preferred paramagnetic metal ions are Gd (III), Mn (II) and Fe (III), with Gd (III) being especially preferred.

When the radiolabel is a gamma-emitting radioactive halogen, the radiohalogen is suitably chosen from $^{123}$I, $^{125}$I $^{131}$I or $^{77}$Br. A preferred gamma-emitting radioactive halogen is $^{125}$I.

When the radiolabel is a positron-emitting radioactive nonmetal, suitable such positron emitters include: $^{11}$C, $^{13}$N, $^{17}$F, $^{18}$F, $^{75}$Br, $^{76}$Br or $^{124}$I. Preferred positron-emitting radioactive non-metals are $^{11}$C, $^{13}$N, $^{124}$I and $^{18}$F, especially $^{11}$C and $^{18}$F, most especially F.

When the radiolabel is a hyperpolarised NMR-active nucleus, such NMR-active nuclei have a non-zero nuclear spin, and include $^{13}$C, $^{15}$N, $^{19}$F, $^{29}$Si and $^{31}$P. Of these, $^{13}$C is preferred. By the term "hyperpolarized," it is meant enhancement of the degree of polarisation of the NMR-active nucleus over its equilibrium polarisation. The natural abundance of $^{13}$C (relative to $^{12}$C) is about 1%, and suitable $^{13}$C-labelled compounds are suitably enriched to an abundance of at least 5%, preferably at least 50%, most preferably at least 90% before being hyperpolarised. At least one carbon atom of a carbon-containing substituent of the activity-based inhibitor of the present invention may be labeled by being enriched with $^{13}$C, which is subsequently hyperpolarised.

The term "cysteine protease," or "cysteine peptidase," refers to the family of peptidases which have a common catalytic mechanism that involves a nucleophilic cysteine thiol in a catalytic triad. The first step is deprotonation of a thiol in the enzyme's active site by an adjacent amino acid with a basic side chain, usually a histidine residue, e.g., as shown in FIG. 1A. Cysteine proteases have characteristic molecular topologies, which can be seen not only in their three-dimensional structures, but commonly also in the two-dimensional structures. Cysteine proteases are divided into clans (proteins which are evolutionary related), and further sub-divided into families, on the basis of the architecture of their catalytic dyad or triad. The cysteine peptidase family includes papain, cathepsins, caspases, legumain, calpains, etc.

The term "papain family" means, as defined in the MEROPS database, the family C1 in the clan CA. The catalytic residues of family C1 have been identified as Cys and His, forming the catalytic dyad. Two other active site residues are found, a Gln residue preceding the catalytic Cys and an Asn residue following the catalytic His. Family C1 peptidases contribute proteolytic activity to the digestive vacuoles of protozoa and to the lysosomal system of eukaryotic cells, specific examples of lysosomal enzymes including cathepsin B (C01.060), cathepsin L (C01.032), cathepsin S (C01.034), cathepsin K (C01.036), cathepsin H (C01.040) and dipeptidyl-peptidase I (C01.070).

The papain family includes "human cysteine cathepsin," which is an enzyme, which is part of the human cysteine cathepsin family, which comprises 11 genes (cathepsins B, C, H, F, K, L, O, S, V, W, and X/Z), as well as mutants of such enzymes. In certain aspects, only cathepsins in the papain family are to be included.

The term "caspase" means a group of enzymes classified in MEROPS as family C14. It is in Clan CD, which contains five families of endopeptidases. Enzymes in the caspase family include CED-3 peptidase; caspase-3; caspase-7; caspase-6; caspase-2; caspase-4; caspase-5; caspase-8; caspase-9; caspase-10; caspase-11; caspase-12; caspase (insect 1); caspase (insect 2); caspase-13; and caspase-14.

The term "legumain" means a lysosomal protease, and a member of the MEROPS C13 family of cysteine proteases. Legumain is evolutionarily conserved and is present in plants, invertebrate parasites, as well as in mammals. Legumain is a member of clan CD, which also includes caspases. An example of an amino acid sequence for a preproprotein of a human legumain can be found in the National Center for Biotechnology Information (NCBI) database (http://www.ncbi.nlm.nih.gov/) at accession number NP 005597 (gi: 21914881

Overview

Multiple types of degradative enzymes, including cathepsins of the cysteine protease family, have been implicated in the regulation of angiogenesis and invasion during cancer progression. Increased expression and activity as well as altered localization of several of these proteases are associated with tumor progression and metastatic potential. While this family of proteases has the potential to be used as a biomarker for disease, currently there are no radiological imaging agents available for these important molecular targets. Described below is a positron emission tomography (PET) radionuclide labeled activity based probe that selectively targets the human cysteine cathepsins B and L, illustrated in FIG. 1C as "Z-FK(DOTA)-AOMK," chelated with a positron emitter. This probe makes use of the highly selective acyloxymethyl ketone (AOMK) functional group to irreversibly label the active site cysteine of papain family proteases. Conjugation of 1,4,7,10-tetraazacyclododecane-1,4,7,10-tetraacetic acid to a dipeptide-AOMK provided a probe that could be efficiently labeled with $^{64}$Cu for PET imaging studies. Biodistribution and microPET imaging using $^{64}$Cu-Z-FK (DOTA)-AOMK was investigated in nude mice bearing subcutaneous tumors expressing either low or high levels of cysteine cathepsin activity. The extent of probe uptake by tumors correlated with overall protease activity and microPET imaging studies confirmed that tumors with high cysteine protease activity could be visualized with good tumor to contralateral background contrast. Taken together these results demonstrate that small molecule activity based probes carrying radio-tracers can be used to image protease activity in living subjects.

The cysteine cathepsins are potentially valuable molecular target for tumor imaging because of their significant function in tumor progression, invasion and metastasis. Although NIRF (Near Infrared Fluorescence) labeled probes that target this class of protease have been successfully applied to optical imaging applications (e.g., Joyce et al., *Cancer Cell*, supra), radioactive probes have not been developed. Part of the reason for the lack of probes for radiological imaging applications is that it is very difficult to design radioactive probes based on protease substrates. Since there is no way to facilitate quenching of the radiolabel and because substrates diffuse away from the protease activity, it is virtually impossible to develop reagents based on peptide substrates.

The highly selective activity based probes disclosed herein covalently target the cysteine cathepsins in order to prepare new PET agents. The main disadvantage of using an inhibitor-based approach is the lack of amplification of signal that is obtained with substrate-based approaches. However, the high expression of cysteine cathepsins in tumor tissue (for example, 6.6 μg CB/mg protein in transitional cell carcinoma, as described in Eijan A M, Sandes E O, Riveros M D, Thompson S, Pasik L, Mallagrino H, Celeste F, Casabe A R., "High expression of cathepsin B in transitional bladder carcinoma correlates with tumor invasion," *Cancer,* 2003; 98: 262-8), and the prior validation of these probes in optical imaging applications suggested that they would be potentially valuable for use in PET imaging.

The present invention utilizes the acyloxymethyl ketone (AOMK) scaffold for a PET probe. Conversion of the Z-FK-AOMK probe to the corresponding DOTA labeled analog Z-FK(DOTA)-AOMK (FIG. 1C) allowed labeling with $^{64}$Cu. We selected $^{64}$Cu as a PET radiolabel because it can be readily produced using a medical cyclotron and the intermediate half-life of $^{64}$Cu makes it suitable for small molecules and peptides radiolabeling.[34, 35] Overall labeling and biodistribution studies with $^{64}$Cu-Z-FK(DOTA)-AOMK indicated that the probe showed rapid clearance in blood but accumulated in tumor tissues with reasonable signal levels. In addition, the probe could also differentiate two tumors (C2C12/Ras and MDA-MB-435) with different levels of cysteine cathepsin activity. C2/C12/Ras cells express high levels of cathepsins and MDA-MB-435 cells express low levels of cathepsin.

As described below, a relatively high uptake of the probe Z-FK(DOTA)-AOMK was observed in tumor tissues, but there was not observed a significant difference in uptake for the C2C12/Ras tumors relative to the MDA-MB-435 tumors at 2 h and 24 h p.i. (for example: C2C12/Ras: 0.30±0.03% ID/g at 2 h vs. 0.27±0.05% ID/g) suggesting that there may still be some degree of non-specific uptake of the probe by the tumors. This non-specific accumulation of the probe is possibly due to its lipophilicity (HPLC retention time=30.9 min; log P=−0.10±0.04). However, we did observe significant differences in the micro-PET signals in the MDA-MB-435 and C2C12/Ras tumors in vivo. Clearly, further modification and optimization of this first generation probe will be required to prepare PET probes with clinical potential. Future work will be aimed at using library approaches to diversify the peptide backbone of the probe to identify compounds with optimal potency, specificity, tumor uptake and in vivo pharmacokinetic properties.

MicroPET imaging studies demonstrated that the C2C12/Ras tumor could be clearly visualized with good tumor to contralateral background contrast at 2 and 24 hrs. post injection. Lower tumor uptake and poor tumor to normal tissue contrast in MDA-MB-435 tumor was observed.

We also observed relatively high accumulation of $^{64}$Cu-Z-FK(DOTA)-AOMK in the liver for both the C2C12/Ras and MDA-MB-435 tumor models (Table 1 and FIGS. 3A and 3B). The release of free $^{64}$Cu from the radiolabeled compound upon decomposition in the blood or transchelation to other proteins may be responsible for this high liver uptake. Alternative chelation systems for $^{64}$Cu such as disclosed here, e.g., cross-bridged cyclam ligands may improve the metal-chelate stability and subsequently improve the biodistribution of the probes, see Sun X, Kim J, Martell A E, Welch M J, Anderson C J, "In vivo evaluation of copper-64-labeled monooxo-tetraazamacrocyclic ligands," *Nucl Med Biol*, 2004; 31: 1051-9, and Boswell C A, Sun X, Niu W, Weisman G R, Wong E H, Rheingold A L, Anderson C J., "Comparative in vivo stability of copper-64-labeled cross-bridged and conventional tetraazamacrocyclic complexes," *J Med Chem*, 2004; 47: 1465-74. An example of such a chelator is the polyazamacrocycle cyclam 1,4,8,11-tetra azacyclo tetradecane, which is known to form thermodynamically and kinetically stable complexes with $^{99m}$Tc.

Since cysteine cathepsins are highly expressed in liver, kidney, and spleen, we expect that some degree of 'background' labeling in normal tissue will always be observed. However, it should be noted that the radioactivity in liver decreased significantly more rapidly than in the tumor tissues suggested that at least part of this signal was due to non-target mediated effects or modification of short-lived proteins. Regardless of these potential issues, the use of position emitting labels allows application of tomographic methods that can resolve signals in specific locations that are free from high protease background. In addition, unlike the NIRF versions of these ABPs the PET probes have the potential to be used to image tissues at much greater depths and with higher overall resolution.

Described below as illustrative of the present invention is a first demonstration of the use of an activity dependent probe (AOMK) bearing a radiolabel as a PET tracer for cysteine cathepsin targeted tumor imaging. Numerous studies have demonstrated that the cysteine cathepsins play an important role in tumor biology as well as in a number of other important human disease pathologies. Therefore, cathepsin-targeted PET imaging agents should find broad applications in the clinic if such agents become available to the nuclear medicine community. Their usefulness in the evaluation of prognosis, as well as in the stratification of cancer patients for cathepsin-targeted drug therapy can be easily envisioned.

Probe Structures

The present probes may be defined according to formulas as set forth below.

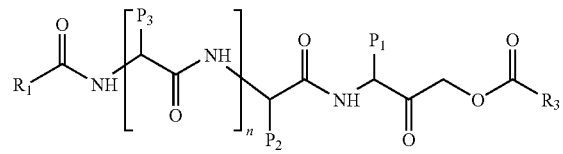

Formula I

Where n, $R_1$, $R_3$, $P_1$, $P_2$, $P_3$ and $P_4$ are as defined above. For purposes of exemplification and clarification, it should be understood that $P_1$, $P_2$ and $P_3$ indicate amino acid side chain positions, $R_1$ and $R_3$ are substituted aryl groups, and one of $P_1$, $P_2$, $R_1$ and $R_3$ bear a radiolabel, and are further as exemplified below:

With regard to Formula I, it will be apparent that, if n is one, there will be a $P_3$, if n is 2, there will be a $P_3$ and $P_4$; if n is zero, there will be no $P_3$, only $P_2$. These variations are further illustrated in Formulas II and III below:

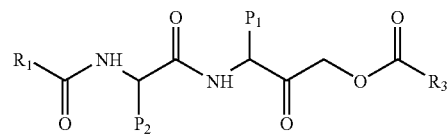

Formula II

Where n=0.

In addition, the present probes may be defined according to a Formula III, containing a related structure with a $P_4$ position:

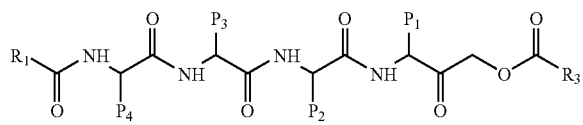

Formula III where n=2.

In the above Formulas I-III, the present stable in vivo cathepsin, legumain or caspase-targeting probes are illustrated according to the AOMK core, having the structure illustrated between $P_1$ and $R_3$. The end groups $R_1$ and $R_3$ are each preferably an aryl group such as 2,6 dimethyl benzyl or other substituted aryl such as 2-nitro, 3-hydroxy aryl. The references to $P_1$ and $P_2$ are substitution points for amino acid side chains. The chelator and/or label may be attached at R1, the part of the molecule that binds to the enzyme, or at $P_1$ or $P_3$. $P_1$ may be for example aspartate; $P_2$ may be for example proline (in which case an additional bond to the adjacent amino group would be present, as shown in Formula IV, below).

In addition, a fourth amino acid $P_4$ may be used, as shown in Formula III above, equivalent to the case where n=2 in Formula I. In Formula I, Formula II, and Formula III, the radiolabel may be present at an amino acid side chain $P_1$-$P_4$, or on the capping group which does not bind to the cysteine cathepsin, namely $R_1$.

The above formulas contain definitions of the groups $P_1$-$P_4$, $R_1$ and $R_3$ as set forth below, with the additional limitation that one of the groups $P_1$-$P_4$ and $R_1$ contains a chelator and/or a radiolabel.

As further exemplification, Formula IV below represents a $P_1$, $P_2$, $P_3$ embodiment with Asp (D) in $P_1$, proline in $P_2$, an aryl side chain (e.g., Phe, Trp, Tyr) in $P_3$ and $R_1$ and $R_3$ groups based on benzyl moieties.

In Formula IV, X is the radiolabel or chelator, it can be considered as attached to an artificial $P_1$ side chain, which may be regarded as a modified lysyl.

Further with regard to amino acid side chains $P_1$ through $P_4$, for purposes of illustration, the following natural amino acid structures are set forth (where * indicates binding to the α-carbon):

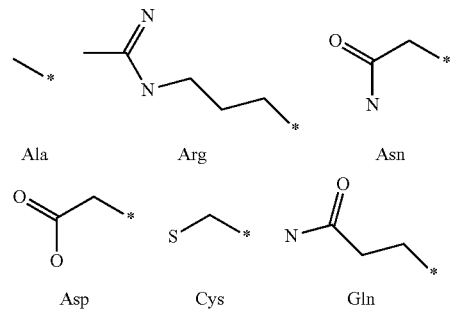

Ala  Arg  Asn

Asp  Cys  Gln

Formula IV

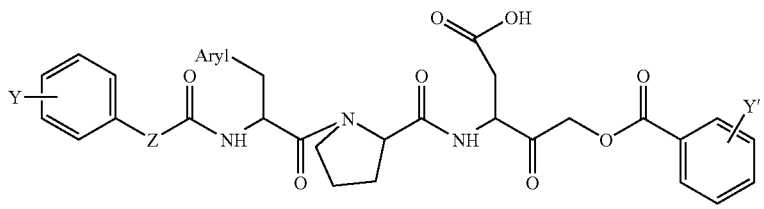

In Formula IV, the chelator/radiolabel is attached at, e.g., Y, Y' or to the Asp residue. Z may be C or O or an alkyl (preferably lower alkyl) or alkoxy (preferably lower alkoxy) linker.

In general, in the above Formulas I-IV, $R_1$ and $R_3$ are capping groups, which are selected for ease of synthesis and compound stability; $P_1$ though $P_4$ are natural and non-natural amino acid side chains; and a chelator is used to bind a radiolabel. The chelator may be a separate moiety such as a macrocyclic compound ligated to a side chain, or may be engineered into the peptide, e.g., as described in U.S. Pat. No. 5,618,513 to Srinivasan, issued Apr. 8, 1997, entitled "Method for preparing radiolabeled peptides," which describes using polyaminocarboxylate ligands formulated with suitable protecting groups such that they can be added to peptides by standard solid phase or solution phase peptide synthetic chemistry.

The capping groups in general may be independently H, NH2, aminocarbonyl, aryl, substituted aryl (including 2-nito, 3-hydroxy phenyl), amino, aminocarbonyl, lower alkyl, cycloalkyl, or a radiolabel; The capping groups may comprise one or two substituent groups on their rings, e.g., methyl, ethyl, methoxy, hydroxyl, nitro, or amino. The side chains are independently amino acid side chains selected from naturally occurring amino acid side chains and those listed in FIG. 4; a chelator or a radiolabel is linked to a capping group or a side chain;

The chelator may be a macrocyclic molecule such as DOTA with a bound radionuclide such as, for example, $^{111}$In, $^{64}$Cu, $^{86}$Y $^{123}$I, $^{131}$I, $^{99m}$YC or $^{68}$Ga, coordinated to its nitrogen atoms, as is known in the art. Preferred radionuclides are those useful for PET imaging.

$R_1$ is preferably linked through an oxygen in the case of cathepsin probes; $R_1$ is linked through a carbon in the case of caspase probes. Examples of capping groups are benzyloxy and benzyl, respectively.

-continued

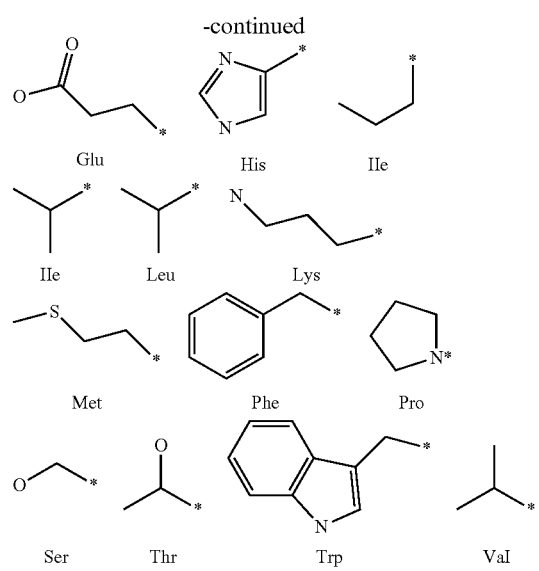

Glu  His  Ile

Ile  Leu  Lys

Met  Phe  Pro

Ser  Thr  Trp  Val

Figure 2A:
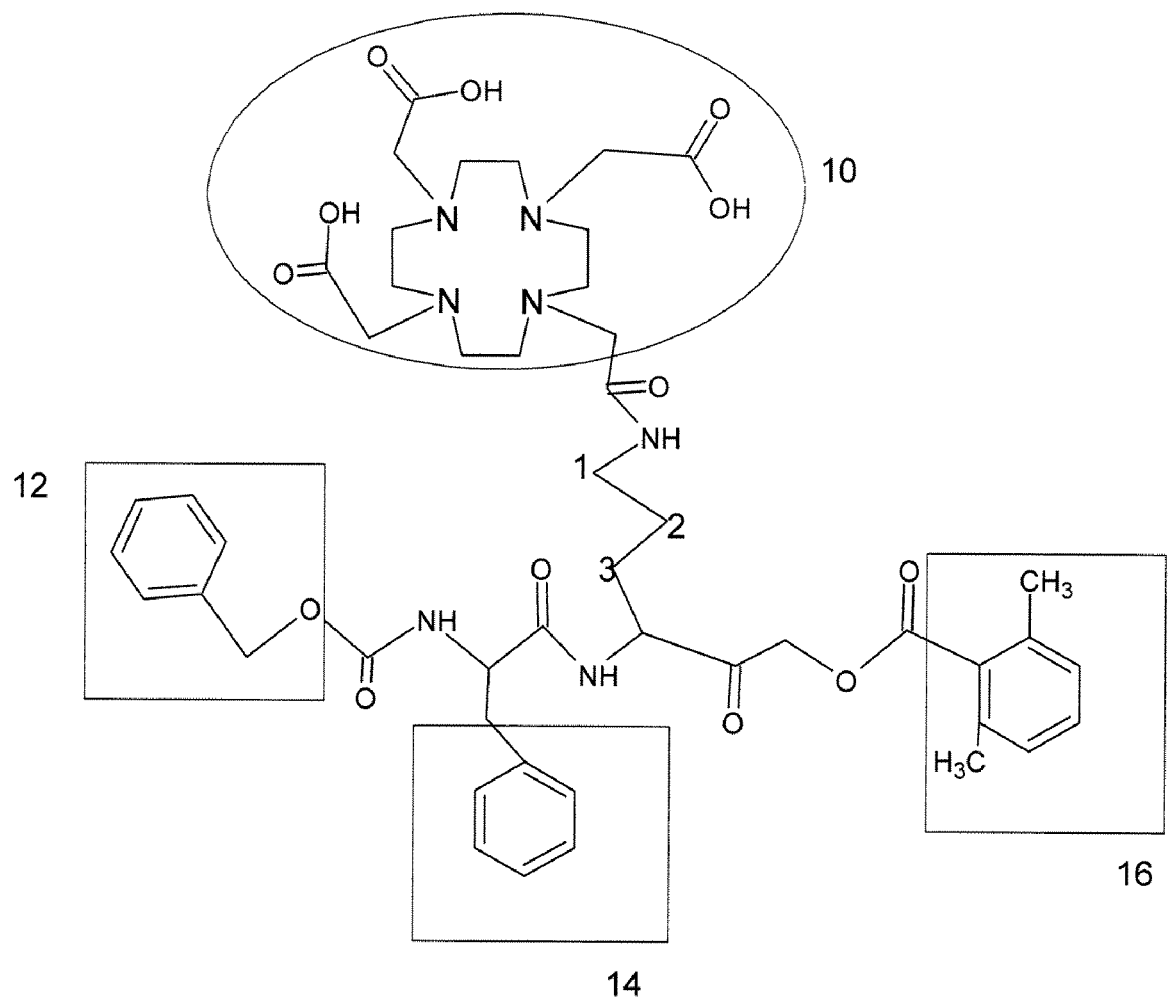
FIG. 2A is a schematic drawing of a chelator—conjugated probe, illustrating several component moieties.

As further exemplification, probes according to the present invention are represented as shown in FIGS. 1, 2 and 4. Possible $P_1$, $P_2$, $P_3$ and $P_4$ groups are shown in FIG. 4. Referring now to FIG. 2A, a probe according to Formula II is shown, with the radiolabel to be attached to a chelator 10 on $P_1$. A DOTA chelator is shown at 10. It is attached at the $P_1$ position through an alkyl (carbons 1, 2, and 3) amide. This is the same structure as Lys, shown above, up to the amino group. An O-benzyl synthetic terminal group is shown at 12, corresponding to $R_1$. This group is added during solid phase synthesis and may be varied without changing activity of the probe. At 14 is shown a phenylalanine amino acid side chain, corresponding to $P_2$. At 16 is shown a dimethyl benzyl cap corresponding to $R_3$ in Formulas I II and III.

The terminology $P_1$-$P_4$ indicates the substrate mimicry of the present probes. Depending on the specificity desired, this side chain may be varied, e.g., as taught in PCT Ser. No. PCT/US 2007/015516, filed 6 Jul. 2007, having inventors in common with this application. As taught there, one may use as an amino acid side chain A, I, W, Y, V or artificial amino acids.

In addition, the side chains in $P_1$ through $P_3$ may be modified chemically and may be synthetic radicals such as shown in FIG. 4. The functional groups present in the amino acid side chains, which can be chemically modified, include amino, carboxylic acid, thiol, guanido, imidazole and hydroxyl groups. Using phenylalanine as an example, a variety of modifications to the side chain are available, some of which are represented in U.S. Pat. No. 5,424,186. Non-natural amino acids are further described in PCT/US2007/015516, filed on 6 Jul. 2007, entitled "Selective Caspase Inhibitors," and naming as co-inventors Bogyo and Berger. In addition, the amino acids of the peptides of the present invention may also be modified. For example, amino groups may be acylated, alkylated or arylated. Benzyl groups may be optionally substituted, e.g., halogenated, nitrosylated, alkylated, sulfonated or acylated.

The following residues are preferred for use in the present selective inhibitors at one or more of $P_1$, $P_2$, $P_3$ or $P_4$: aspartate, valine, glutamate, threonine, proline, leucine, isoleucine, and phenylalanine, as well as specified non-natural side chains 3, 6, 8, 23, 26, 29, 31, 34, 38 of FIG. 4. Selectivity may be determined by testing with different cysteine proteases as described above. The natural side chains may be further modified. For example, one may use chemically modified amino acids may be incorporated into the present compounds:

Acetylated
  N-acetyl-L-alanine, N-acetyl-L-arginine; N-acetyl-L-asparagine; N-acetyl-L-aspartic acid;
  N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine;
  N-acetyl-L-threonine; N-acetyl-L-tryptophan; N-acetyl-L-tyrosine; N-acetyl-L-valine.
Amidated
  L-alanine amide, L-arginine amide
Formylated
  N-formyl-L-methionine
Hydroxylated
  4-hydroxy-L-proline
Methylated
  N-methyl-L-alanine, N,N,N-trimethyl-L-alanine, omega-N, omega-N-dimethyl-L-arginine, L-beta-methylthioaspartic acid, N5-methyl-L-glutamine, L-glutamic acid 5-methyl ester, 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine.
Phosphorylated
  Omega-N-phospho-L-arginine, L-aspartic 4-phosphoric anhydride, S-phospho-L-cysteine 1'-phospho-L-histidine, 3'-phospho-L-histidine, O-phospho-L-serine, O-phospho-L-threonine O4'-phospho-L-tyrosine.
Other
  2'-[3-carboxamido-3-(trimethylammonio)propyl]-L-histidine (diphthamide)N6-biotinyl-L-lysine N6-(4-amino-2-hydroxybutyl)-L-lysine (Hypusine)

Thus it is to be understood that, for example, "A" refers to naturally occurring Ala, but may also include amidated Ala, as exemplified in the table above. The following amino acids are known to be similar and therefore may be useful in preparing active derivatives of the exemplified compounds. To be "active," a derivative should have a Ki(app) of at least 500,000, preferably at least 1,000,000. The following substitutions are based on D. Bordo and P. Argos, Suggestions for "Safe" Residue Substitutions in Site-Directed Mutagensis, *J. Mol. Biol.* 217 (1991) 721-729:

A—S, K, P, E
D—N, E
E—D, Q, A
F—Y
I—V, L
L—I, V
P—A
T—S, K
V—I, L

Preferred imaging agents do not undergo facile metabolism in vivo, and hence most preferably exhibit a half-life in vivo of 60 to 240 minutes in humans. The imaging agent is preferably excreted via the kidney (i.e., exhibits urinary excretion). The imaging agent preferably exhibits a signal-to-background ratio (that is, binding at the site of active enzyme only) of at least 1.5, most preferably at least 5, with at least 10 being especially preferred. When the imaging moiety is radioactive, clearance of one half of the peak level of imaging agent which is either non-specifically bound or free in vivo, preferably occurs over a time period less than or equal to the radioactive decay half-life of the radioisotope. Furthermore the preferred imaging and binding agents will be specific for a known member or members of the cysteine protease family. For example, AB53 specifically targets caspase-3, and GB111 is directed towards cathepsin L. The preferred imaging agent will also have the ability to penetrate cells, which ability is conferred by adding appropriate charged and hydrophobic moieties, such as an aromatic radical (e.g. naphthalene, quinoline, isoquinoline, etc.) having charged substituents (e.g. $SO_3$, $NO_2$, etc.)

The imaging agent will have a high degree of binding to the target enzyme, which may be measured in terms of its ability to inhibit active enzyme. It will have an IC50 of less than about 100 nM, preferably less than about 20 nM.

The inhibitors may be targeted to specific caspases, such as illustrated in the following table, taken from the above referenced Serial No.: PCT/US2007015516; Filed: Jul. 6, 2007

TABLE 1

| Primary Target | Compound name | P4 | P3 | P2 |
| --- | --- | --- | --- | --- |
| Caspase 3, 7, 8, 9 | AB28 | 6 | E | 8 |
| " | AB11 | D | E | P |
| Caspase 3, 7 | AB06 | D | 3 | V |
| " | AB13 | D | 34 | V |
| " | AB12 | D | 29 | V |
| Caspase 8 | AB20 | 29 | E | T |
| " | AB19 | 31 | E | 23 |
| " | AB18 | 31 | E | T |
| Caspase 9 | — | L | E | H |
| " | AB38 | P | L | A |
| " | AB42 | I | F | P |
| " | AB41 | I | L | 38 |

The designations for $P_2$, $P_3$ and $P_4$ are given in FIG. 4. $P_1$ is D. Representative structure AB 28 is as follows:

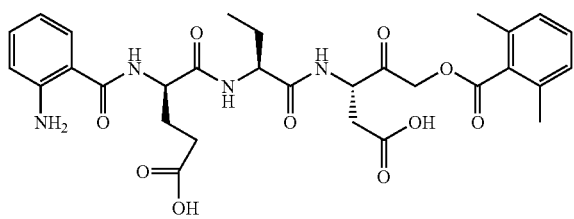 [SMILES: CC[C@H](NC(=O)[C@@H](CCC(=O)O)NC(=O)c1ccccc1N)C(=O)N[C@@H](CC(=O)O)C(=O)COC(=O)c1c(C)cccc1C]

AB11 is as follows

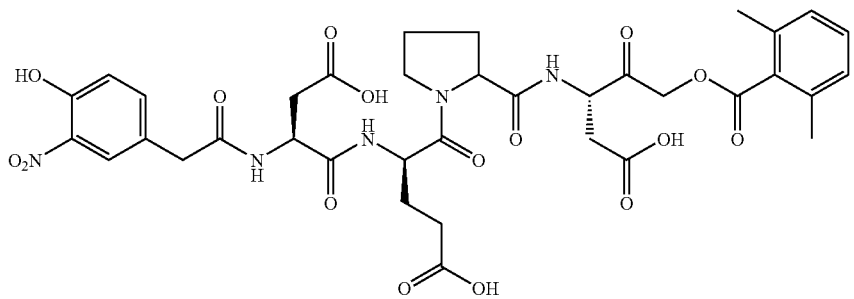 [SMILES: Cc1cccc(C)c1C(=O)OCC(=O)[C@H](CC(=O)O)NC(=O)C1CCCN1C(=O)[C@@H](CCC(=O)O)NC(=O)[C@H](CC(=O)O)NC(=O)Cc1ccc(O)c([N+](=O)[O-])c1]

As can be see, there are in each compound groups available for chelation and labeling with a radiolabel. These include the $R_1$ amino or nitro group and the $P_3$ or $P_4$ group is COOH.

PET Imaging

Positron emission tomography (PET) is a nuclear medicine medical imaging technique, which produces a three-dimensional image or map of functional processes in the body. The system detects pairs of gamma rays emitted indirectly by a positron-emitting radioisotope, which is introduced into the body. To conduct the scan, a short-lived radioactive tracer isotope, which decays by emitting a positron, which also has been chemically incorporated into a metabolically active molecule (in this case a molecule which binds specifically to active cathepsin) is injected into the circulation. There is a waiting period while the labeled molecule becomes concentrated in tissues of interest; then the research subject or patient is placed in the imaging scanner. The molecule most commonly used for this purpose is fluorodeoxyglucose (FDG), a sugar, for which the waiting period is typically an hour.

As the radioisotope undergoes positron emission decay (also known as positive beta decay), it emits a positron, the antimatter counterpart of an electron. After traveling up to a few millimeters the positron encounters and annihilates with an electron, producing a pair of annihilation (gamma) photons moving in opposite directions. These are detected when they reach a scintillator material in the scanning device, creating a burst of light, which is detected by photomultiplier tubes or silicon avalanche photodiodes (Si APD).

MicroPET imaging can be carried out using commercially available equipment. For example, in the examples below, an instrument from Concorde Microsystems, Inc. was used. The microPET Primate 4-ring system (P4) is an animal PET tomograph with a 7.8 cm axial extent, a 19 cm diameter transaxial field of view (FOV) and a 22 cm animal port. The system is composed of 168 detector modules, each with an 8×8 array of 2.2×2.2×10 mm3 lutetium oxyorthosilicate crystals, arranged as 32 crystal rings 26 cm in diameter. The detector crystals are coupled to a Hamamatsu R5900-C8 PS-PMT via a 10 cm long optical fiber bundle. The detectors have a timing resolution of 3.2 ns, an average energy resolution of 26%, and an average intrinsic spatial resolution of 1.75 mm.

Human whole body PET scanning is available at a number of radiology centers. In this case, the patient receives an injection of labeled probe in a vein in the arm and images are obtained approximately one hour after the injection. The scan requires about 60 minutes in order to generate satisfactory images. The patient lies motionless on a bed while, for most patients, images are made from the neck to the mid-thigh, depending on the site of the tumor to be imaged. The scanner does not generally completely cover the patient's face.

A composition of the present invention comprises one of the aforementioned radiolabeled activity-based probes and a carrier such as a physiological buffered saline solution or a physiologically buffered sodium acetate carrier. It is contemplated that the composition will be systemically administered to the patient as by intravenous injection. It should therefore be essentially sterile and free of pyrogens and other toxic materials. Suitable dosages for use as a diagnostic imaging agent will depend on the particular tumor and/or organ of interest. For example, one may use from about 0.2 to about 2.0 mCi of radiolabel for the adrenal medulla or tumors therein, and from about 2.0 to about 10.0 mCi of radiolabel for imaging of the heart and adrenal medulla or tumors therein. For use as a therapeutic agent, a higher dosage is required, for example, from about 100 to about 300 mCi of the material.

Dosages may be calculated depending on the tumor imaging and the radionuclide used. Guidance for dosages may be found in the following references, with the radionuclide indicated: Oyama N. *Nucl Med Biol* 2002; 29:783-790. (Washington University, C-11 acetate), Inubushi M. *Eur J Nucl Med Mol Imaging*, 2004; 31:110-116 (N-13 NH3), Green L A J *Nucl Med*, 1998: 39:729-734 (F18 FDG), Zingone A. *Life Sciences*, 2002; 71:1293-1301 (F-18 FDG), and Zanzoko P. *Eur J Nucl Med*, 2004; 31: 117-128 (I-124).

Radiolabels for Positron Emission Tomography (PET) include primarily [18]F. However, other positron emitting radionuclides can be prepared in high yields in small biomedical cyclotrons. Some of these have half-lives that make delivery significantly easier than the delivery of $^{18}$F compounds. These radionuclides include: [64]Cu (half life 12.7 h), [76]Br (half life 16.2 h), [86]Y (half life 14.74 h) [55]Co (half life 17.5 h), and [124]I (half life 4.2 days). Chen et al., "MicroPET and Autoradiographic Imaging of Breast Cancer αv-Integrin Expression Using [18]F- and [64]Cu-Labeled RGD Peptide," *Bioconjugate Chem.*, 15 (1), 41-49, 2004, gives further information in the preparation and use of labeled peptides, which may be applied to the present probes according to the guidance presented here. In that case, the authors wished to visualize and quantify integrin expression. Here, in contradistinction, it is desired to visualize and quantify specific caspase expression, e.g., caspase 3, 7, 8, or 9, without background from inactive caspases or other cysteine proteases. However, the guidance given in that publication may be adapted given the present teachings to $^{64}$Cu labeled cysteine protease probes as described herein. The authors conjugated c(RGDyK) with 1,4,7,10-tetraaza-1,4,7,10-tetradodecane-N,N',N,N'''-tetraacetic acid (DOTA) and labeled the DOTA-RGD conjugate with $^{64}$Cu (t1/2=12.8 h, 19%+) in high radiochemical purity and specific activity. A variety of water soluble chelators may be used, e.g., diethylenetriaminepentaacetic acid (DTPA), ethylenediaminetetraacetic acid (EDTA), 1,4,7,10-tetraaza-cyclododecane-N,N',N'',N'''-tetraacetate (DOTA), tetraaza-cyclotetradecane-N,N',N'',N'''-tetraacetic acid (TETA), hydroxyethylidene diphosphonate (HEDP), dimercaptosuccinic acid (DMSA), diethylenetriaminetetramethylenephosphonic acid (DTTP) and 1-(p-aminobenzyl)-DTPA, 1,6-diamino hexane-N,N,N',N'-tetraacetic acid, DPDP, and ethylenebis (oxyethylenenitrilo)-tetraacetic acid.

One may also use the cross-bridged tetraamine ligand 4,11-bis(carboxymethyl)-1,4,8,11-tetraazabicyclo[6.6.2]hexadecane ($H_2$CB-TE2A), which allows formation of a radio-copper complex with higher in vivo stability than that of the corresponding non-cross-bridged analog 1,4,8,11-tetraaza-cyclotetradecane-1,4,8,11-tetraacetic acid (TETA). See, Boswell, et al., "Optimization of labeling and metabolite analysis of copper-64-labeled azamacrocyclic chelators by radio-LC-MS," *Nuclear Medicine and Biology* 32 (2005) 29-38. The term "macrocyclic ligands," referred to above, is also used to describe compounds such as H2CB-TE2A, $H_2$CB-DO2A, H4TETA and H4DOTA.

The present methods and compositions are also useful in SPECT imaging, which employs isotope tracers that emit high-energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $^{123}$I, a γ-emitter with a 13.3 hour half-life. Compounds labeled with $^{123}$I can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Other isotopes can serve for SPECT (single photon emission computed tomography) imaging. SPECT imaging employs isotope tracers that emit high energy photons (gamma-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $^{123}$I, a gamma emitter with a 13.3 hour half-life. Other halogen isotopes can serve for PET or SPECT imaging, or for conventional tracer labeling. These include $^{75}$Br, $^{76}$Br, $^{77}$Br and $^{82}$Br as having usable half-lives and emission characteristics. Further information on PET labels may be found in US 20040131544 by MacLean, et al., published Jul. 8, 2004, entitled "In vivo imaging."

Gamma labels are further contemplated. Cuntz et al., "Intraoperative gamma detection of $^{125}$I-lanreotide in women with primary breast cancer," *Annals of Surgical Oncology*, Vol 6, Issue 4 367-372, 1999, discloses the use of $^{125}$I for intraoperative tumor-gamma detection using a radiolabeled somatostatin analog. The present The Kato et al. paper described above sets forth experimental guidance for $^{125}$I labeling. As reported there, a 1.5 mL microcentrifuge tube is coated with 100 mg of IODO-GEN® (Pierce, Rockford, Ill.). The AOMK probe (62.5 µl of a 0.2 mM solution in phosphate buffer pH 7.4) is added to the tube. Na $^{125}$I (1 mCi, 10 ml) is added to the tube and incubation continued for 20 min. Labeled inhibitor is purified by application to a Sep-Pak® (Waters, Milford, Mass.) column containing a $C_{18}$ stationary phase. After sample application, the column is washed with 25 mL of phosphate buffer pH 7.5. Labeled inhibitor is eluted using 100% acetonitrile. Fractions of 1 mL are collected and samples with the largest number of counts are pooled and used without further purification. 99MTechnetium may also be used as a radiolabel and detected with a gamma camera. Labeling of a peptide with 99MTechnetium is further described in U.S. Pat. No. 5,780,007, "Technetium-99m labeled peptides for imaging."

Targeting of Probes Towards Specific Cysteine Proteases

As described above, the present probes are directed to human cysteine cathepsins, caspases or legumain. Cysteine cathepsins were selected as in vivo activity-based imaging because, as described above, they are implicated in tumorigenesis and invasion. Caspases are useful in imaging apoptosis. Legumain is highly expresses in several types of tumors. Legumain expression is also associated with increased cancer cell invasion and metastasis. Legumain expression is also associated with reduced cancer cell apoptosis. Thus different cysteine cathepsins are individually involved in a number of physiological processes, and it is advantageous to create probes specific to a given cysteine protease enzyme. For example, imaging of active caspases, but not cathepsin, is useful in studies of apoptosis, as these enzymes may be found in neuronal cells, apoptosis of macrophages and smooth muscle cells in atherosclerotic lesions, and in acquired immunodeficiency syndrome, cancer, myelodysplastic syndromes, ischemia/reperfusion injury, and autoimmune disorders. One may also direct the present activity based probes specifically to legumain. See, *Bioorganic & Medicinal Chemistry Letters*, Volume 17, Issue 3, 1 Feb. 2007, pages 649-653. Directing the present probes to a specific target, as described below, may be accomplished by choice of $P_1$-$P_4$ residues, and by a linkage of the $R_1$ group. It has been found that a proline in the $P_2$ position directs the selectivity of the probe away from cathepsin B, and a bulky group in the $P_3$ position directs activity away from legumain, leaving specific reactivity against caspase-3. Caspase targeting also favors a D in the $P_1$ position. A C linkage rather than an O linkage to the $R_1$ capping group is also found in caspase-selective probes.

EXAMPLES

Example 1

Preparation of Labeled Probes

Preparation of AOMK inhibitors: 1,4,7,10-tetraaazacyclododecane-1,4,7,10 tetraacetic acid conjugated AOMK analog [Z-FR-AOMK in FIG. 1C] was prepared by methods similar to those previously described by the present inventors. See, Reference 30 US PGPUB 2007/0036725 by Bogyo, et al., published Feb. 15, 2007, entitled "Imaging of protease activity in live cells using activity based probes." Methods for preparation of Z-FR-AOMK are also given in Kato et al., "Activity-based probes that target diverse cysteine protease families," nature *Chem. Biol.* 1:33-38 (2005). The synthesis was carried out using a combination of solid and solution phase chemistries. This synthetic route was chosen over recently reported solid-phase methods due to the formation of an intra-molecular acyl transfer reaction on resin that was observed when an aliphatic acyloxy group was used in place of the 2,6-dimethyl benzoic acid group. The fully protected carboxyl benzoyl capped phenylalanine-lysine di-peptide was synthesized using standard solid phase peptide synthesis and was converted to the corresponding bromo-methyl ketone in solution. Coupling of 2,6-dimethyl benzoic acid with the BMK resulted in the AOMK intermediate. Conversion of the BMK using N-trityl protected glycine yielded the AOMK that was coupled to the commercially available QSY7 quenching group after removal of the trityl group. Finally, removal of the Boc protecting group on the sidechain of lysine allowed attachment of the radiolabel.

DOTA Preparation: DOTA was obtained from Macrocyclics Inc. (Richardson, Tex.). All other chemicals were obtained from Sigma-Aldrich Chemical Co. (St. Louis, Mo.). AOMK analog, Z-FK-AOMK was first prepared as described above. $^{64}$Cu was provided by the Department of Medical Physics, University of Wisconsin at Madison (Madison, Wis.). A CRC-15R PET dose calibrator (Capintec Inc., Ramsey, N.J.) was used for all radioactivity measurements. Reverse phase high performance liquid chromatography (RP-HPLC) was performed on a Dionex Summit HPLC system (Dionex Corporation, Sunnyvale, Calif.) equipped with a 170U 4-Channel UV-Vis absorbance detector and radioactivity detector (Carroll & Ramsey Associates, model 105S, Berkeley, Calif.). UV detection wavelengths were 218 nm, 254 nm and 280 nm for all the experiments. Both semi-preparative (Vydac, Hesperia, Calif. 218TP510-C18, 10 mm×250 mm) and analytical (Dionex, Sunnyvale, Calif. Acclaim120 C18, 4.6 mm×250 mm) RP-HPLC columns were used. The mobile phase was solvent A, 0.1% trifluoroacetic acid (TFA)/H$_2$O, and solvent B, 0.1% TFA/acetonitrile. Matrix-assisted laser desorption/ionization time of flight mass spectrometry (MALDI-TOF-MS) were performed on a Perseptive Voyager-DE RP Biospectrometry instrument (Framingham, Mass.) by the Stanford Protein and Nucleic Acid Biotechnology Facility. Alpha cyano-4-hydroxy-cinnamic acid (α-CHCA, prepared as 10 g/L in 33.3% CH$_3$CN: 33.3% EtOH: 33.3% H$_2$O: 0.1% TFA) were used as the solid matrix. Tumorigenic murine skeletal myoblast cell line C2C12/Ras (retrovirally transduced with the ras oncogene) was a generous gift from Dr. Helen Blau, Stanford University, CA, and human breast cancer MDA-MB-435 cells were obtained from the American Type Tissue Culture Collection (Manassas, Va.). Female athymic nude mice (nu/nu) were purchased from Charles River Laboratories (Boston, Mass.).

Conjugation of Chelator: DOTA was conjugated with the Z-FR-AOMK as prepared above in a manner similar to that described in Cheng Z, Xiong Z, Subbarayan M, Chen X, Gambhir S S. $^{64}$Cu Labeled Alpha-Melanocyte Stimulating Hormone Analog for microPET Imaging of Melanocortin, Receptor Expression. *Bioconjug Chem*, 2007; [Epub ahead of print].

Briefly, DOTA, 1-ethyl-3-[3-(dimethylamino)propyl]carbodiimide (EDC), and N-hydroxy-sulfonosuccinimide (SNHS) at a molar ratio of 1:1:0.8 were mixed and incubated at 4° C. for 30 min (pH=5.5). Z-FR-AOMK was then added to the in situ prepared sulfosuccinimidyl ester of DOTA (DOTA-OSSu) in a theoretic stoichiometry of 5:1. The reaction solution was mixed and reacted at 4° C. overnight (pH 8.5-9.0). The resulting Z-FK(DOTA)-AOMK (See FIG. 1C) conjugate was then purified by HPLC on a semipreparative C-18 column. The flow rate was 3 mL/min, with the mobile phase starting from 95% solvent A and 5% solvent B (0-3 min) to 35% solvent A and 65% solvent B at 33 min, then going to 85% solvent B and 15% solvent A (33-36 min), maintaining this solvent composition for another 3 min (36-39 min) and returning to initial solvent composition by 42 min. Fractions containing the product were collected and lyophilized. The target product was characterized by MALDI-TOF-MS and ready for use in the radiolabeling reactions. Z-FK(DOTA)-AOMK was characterized by LC-MS. The measured molecular weight (MW) was consistent with the expected MW: m/z=960.5 for [M+H]$^+$ (C$_{49}$H$_{66}$N$_7$O$_{13}$, Calculated MW=960.5). Non-radioactive $^{nat}$Cu-Z-FK(DOTA)-AOMK was prepared as a reference compound. Its MW was measured as 1021.6 for [M+H]$^+$ (C$_{49}$H$_{64}$CuN$_7$O$_{13}$, Calculated MW=1021.4).

Analytic HPLC was performed on the same HPLC system using a C-18 analytical column and flow rate of 1 mL/min.

Radiolabeling The Z-FK(DOTA)-AOMK conjugate (FIG. 1C) was radiolabeled with $^{64}$Cu ($t_{1/2}$=12.7 h, $E_{\beta^+max}$=656 keV, 19%) at 50° C. for 1 h. The purification of the crude reaction mixture using analytical RP-HPLC afforded $^{64}$Cu-Z-FK(DOTA)-AOMK with >95% radiochemical purity (retention time=30.9 min). The specific radioactivity of $^{64}$Cu-Z-FK(DOTA)-AOMK was determined by analytic radio-HPLC to be over 0.48 Ci/μmol (17.8 MBq/nmol, 500 μCi/μg) at the end of synthesis (EOS). From the octanol-water partition coefficient measurements, the log P value of tracer was determined to be −0.10±0.04. This labeled compound was then used for in vitro and in vivo labeling experiments.

The Z-FK(DOTA)-AOMK was radiolabeled with $^{64}$Cu by addition of 185 MBq (5 mCi)$^{64}$CuCl$_2$ (2 μg compound per 37 MBq $^{64}$Cu) in 0.1 N NaOAc (pH 5.5) buffer followed by a 1 hour incubation at 50° C. The radiolabeled complex was then purified by analytical radio-HPLC. An HPLC radiochromatogram of purified $^{64}$Cu-Z-FK(DOTA)-AOMK showed essentially a single peak (data not shown).

The reaction solution was injected into an analytical radio-HPLC using the same elution gradient and flow rate as the one used in the cold Z-FK(DOTA)-AOMK analysis. Purified radiolabeled peptide was dried by rotary evaporator. The radiolabeled compound was reconstituted in phosphate-buffered saline (PBS) and passed through a 0.22 μm Millipore filter into a sterile vial for in vitro and animal experiments.

The non-radioactive $^{nat}$Cu-Z-FK(DOTA)-AOMK was also synthesized by mixing of Z-FK(DOTA)-AOMK (100 μg, 0.104 μmol) with high-purity natural copper chloride (CuCl$_2$, 21 μg, 0.156 μmol) in 0.1 N NaOAc (pH 5.5) buffer followed by 2 hour incubation at 70° C. The product was purified by HPLC and confirmed by MALDI-TOF-MS.

Octanol/water partition coefficient. To determine the lipophilicity of $^{64}$Cu-Z-FK(DOTA)-AOMK, approximately 370 kBq of $^{64}$Cu-labeled complex in 500 μl of PBS (pH 7.4) was added to 500 μl of octanol in an eppendorf microcentrifuge tube. The resulting biphasic system was mixed vigorously for 10 min and left at room temperature for another 60 min. The two phases were then separated by centrifugation at 2000 g for 5 min (model 5415R Eppendorf microcentrifuge; Brinkman, Westbury, N.Y.). From each layer, an aliquot of 100 μl was removed and counted in a γ-counter (Packard Instruments). The partition coefficient (log P) was then calculated as a ratio of counts in the octanol fraction to the counts in the water fraction. The experiment was repeated 3 times. The lipophilicity of the probe affects its in vivo pharmacokinetics, and should be modest (~0), with hydrophobic and hydrophilic groups present. For further details, see Lin et al., "Role of Pharmacokinetics and Metabolism in Drug Discovery and Development," *Pharmacological Reviews*, Vol. 49, Issue 4, 403-449, December 1997.

Example 2

Labeling Intact Tumor Cells with $^{64}$Cu Labeled ABP

Before applying the radiolabel probe in vivo we first tested the ability of the probe to label multiple tumor cell lines grown in vitro. We initially examined the labeling of the human breast cancer cell line MBA-MB-435 and a mouse myoblastoma cell line that had been transformed by overexpression of the ras oncogene (C2C12/Ras). Both of these cell lines were used for in vivo imaging studies with the NIRF-labeled cysteine cathepsin probes. To confirm earlier studies of these cells using the NIRF probes we labeled them with general Cy5-labeled probe GB123 (FIG. 1C). As previously reported, the cathepsin B and L activity of C2C12/Ras was significantly (7.4 fold) higher than observed for the same targets in the MDA-MB-435 cells. Labeling of the same cells with $^{64}$Cu-Z-FK(DOTA)-AOMK confirmed that the DOTA produced a similar labeling pattern to that observed for the NIRF probe GB123. Again, the highest level of cathepsin activity was observed for cathepsin B with only weak labeling of the heavy and light chain forms of cathepsin L. In addition, the specificity of the Cu-labeled probe for the cysteine cathepsins was confirmed by the complete loss of labeling of the protease targets when cells were pretreated with the general cysteine cathepsin inhibitor JPM-OEt (REF).

This result confirms that the Cu-labeled probe is able to gain access to the lysosomal compartment in intact cells and that it efficiently modifies active cathepsins B and L. It also confirms that the overall specificity and sensitivity is similar to that observed for the validated optical imaging probe GB123.

C2C12/Ras and MDA-MB-435 cells (0.25 M each well) were seeded in a six-well plate one day before the study. Cells were pretreated with the general papain family protease inhibitor JPM-OEt (50 $\mu M^{28}$) or with control DMSO (0.1%) for 1 h and labeled by addition of $^{64}$Cu-Z-FK(DOTA)-AOMK (555 KBq, 15 µCi) to culture medium for 2 h. Cells was then washed with PBS and lysed. Equal amounts of protein per lane were separated by 12% SDS-PAGE. The labeled proteases were visualized by scanning of the gel with a Typhoon 9410 imager (GE Healthcare, Piscataway, N.J.). The labeled bands were quantified with ImageJ 1.36b (public domain software from National Institute of Health).

Example 3

Subcutaneous Tumor Model and Biodistribution Studies

All animal studies were carried out in compliance with Federal and local institutional rules for the conduct of animal experimentation. Female athymic nude mice (nu/nu) were obtained from Charles River Laboratories (Boston, Mass.) at 7-8 weeks old and kept under sterile conditions. The nude mice were inoculated subcutaneously in the right shoulder with $2 \times 10^6$ cultured C2C12/Ras cells or $5 \times 10^6$ MDA-MB-435 cells. When the tumors reach 0.5-0.8 cm in diameter, the tumor bearing mice were subjected to in vivo biodistribution studies. For biodistribution studies, the mice bearing C2C12/Ras or MDA-MB-435 tumor xenografts (n=3 for each group) were injected with 740 KBq (20 µCi) of $^{64}$Cu labeled tracer through the tail vein and sacrificed at different time points post injection (p.i.). Tumor and normal tissues of interest were removed and weighed, and their radioactivity was measured in a gamma-counter. The radioactivity uptake in the tumor and normal tissues was expressed as a percentage of the injected radioactive dose per gram of tissue (% ID/g).

Example 4

MicroPET Imaging

We performed micro PET imaging of mice bearing the MDA-MB-435 and C2C12/Ras tumors. The static microPET images (5 or 10-min scan, three tumor bearing mice were used for each study) of $^{64}$Cu-Z-FK(DOTA)-AOMK are illustrated in coronal images of the subcutaneously implanted tumor-bearing mice (FIG. 3). Although the radioactivity accumulation in the liver and kidney are relatively high, the C2C12/Ras tumor with high cysteine cathepsin activity is clearly visualized with good tumor to contralateral background contrast of 2 and 24 hours post injection (FIG. 3A). In contrast, low tumor uptake and poor tumor to normal tissue contrast in MDA-MB-435 tumor was observed (FIG. 3B). FIG. 3B shows images at 1 hour, 4 hours and 28 hours post injection. The tumor, indicated by the arrow, is not clearly illuminated. This data suggest that while the overall signals are relatively low that reasonable contrast cane be observed for tumors that express high levels of active cysteine cathepsins.

PET imaging of tumor-bearing mice is performed on a microPET R4 rodent model scanner (Concorde Microsystems Inc, Knoxyille, Tenn.). The mice bearing C2C12/Ras and MDA-MB-435 tumors were injected with 5.55 MBq (150 µCi) of $^{64}$Cu AOMK probe via the tail vein. At different times p.i., the mice were anesthetized with 2% isoflurane, and placed in the prone position and near the center of the field of view of microPET. The 5 or 10-min static scans were obtained and the images were reconstructed by a two-dimensional ordered subsets expectation maximum (OSEM) algorithm.

Statistical Method. Statistical analysis was performed using the Student's t-test for unpaired data. A 95% confidence level was chosen to determine the significance between groups, with P<0.05 being significantly different. These methods were used to compare the biodistribution of a probe in the two tumor models used (C2C12/Ras and MDA-MB-435).

Example 5

Biodistribution of $^{64}$Cu-Z-FK(DOTA)-AOMK in Subcutaneous C2C12/Ras and MDA-MB-435 Tumors We next examined the overall biodistribution of $^{64}$Cu-Z-FK(DOTA)-AOMK using athymic nude mice carrying subcutaneously grafted C2C12/Ras and MDA-MB-435 tumors. Uptake of the probe at 0.5, 2, and 24 h p.i. was measured in the C2C12/Ras mouse model, while in the MDA-MB-435 breast cancer model samples were analyzed only at 2 h and 24 h (Table 2). $^{64}$Cu-Z-FK(DOTA)-AOMK displayed rapid blood clearance, resulting in low blood and muscle uptake even at the early time points (30 min p.i.) in both models. Importantly, we observed rapid accumulation of radioactivity in the C2C12/Ras tumors expressing high levels of cysteine cathepsins ($0.35\pm0.13\%$ ID/g at 0.5 h p.i.). This activity remained in the tumors resulting in an uptake of $0.27\pm0.05\%$ ID/g at 24 h p.i. For the MDA-MB-435 tumors with lower cysteine cathepsin expression, tumor uptake was approximately 2 fold lower at each time point relative to the C2C12/Ras tumors (P<0.05). Furthermore, while moderate tumor-to-background ratios (tumor/blood 1.25 and tumor/muscle 5.64 at 2 h p.i.) were observed in the C2C12/Ras tumors, only low tumor-to-background ratios (tumor/blood 0.61 and tumor/muscle 3.03 at 2 h p.i.) were found for the MDA-MB-435 tumors. For both tumor models, $^{64}$Cu-Z-FK(DOTA)-AOMK displayed very low accumulation in most non-tumor tissues. The highest radioactivity was found in the liver due to high endogenous expression of various cysteine cathepsins. Moderate renal accumulation was also observed at all times in both tumor models. However, the relatively low tumor accumulation of $^{64}$Cu-Z-FK(DOTA)-AOMK relative to liver, lung, kidney, stomach and intestines suggests that further modification of this probe will be required to enhance its utility for in vivo applications.

TABLE 2

Biodistribution data of $^{64}$Cu-Z-FK(DOTA)-AOMK in both C2C12/Ras and MDA-MB-435 cancer bearing mouse models.

|  | C2C12/Ras 0.5 h | C2C12/Ras 2 h | C2C12/Ras 24 h | MDA-MB-435 2 h | MDA-MB-435 24 h |
|---|---|---|---|---|---|
| Tumor | 0.35 ± 0.13 | 0.30 ± 0.03 | 0.27 ± 0.05 | 0.18 ± 0.00 | 0.14 ± 0.05 |
| Blood | 0.24 ± 0.07 | 0.24 ± 0.03 | 0.28 ± 0.03 | 0.29 ± 0.01 | 0.28 ± 0.13 |
| Muscle | 0.06 ± 0.01 | 0.05 ± 0.01 | 0.06 ± 0.02 | 0.06 ± 0.00 | 0.06 ± 0.02 |
| Bone | 0.09 ± 0.02 | 0.10 ± 0.01 | 0.14 ± 0.10 | 0.18 ± 0.06 | 0.20 ± 0.20 |
| Heart | 0.25 ± 0.02 | 0.30 ± 0.08 | 0.46 ± 0.07 | 0.43 ± 0.09 | 0.42 ± 0.15 |
| Liver | 3.71 ± 1.04 | 3.59 ± 1.01 | 1.86 ± 0.57 | 2.64 ± 0.08 | 1.37 ± 0.19 |
| Lung | 0.50 ± 0.17 | 0.59 ± 0.22 | 0.65 ± 0.15 | 0.72 ± 0.08 | 0.47 ± 0.08 |
| Kidney | 0.74 ± 0.29 | 0.67 ± 0.19 | 0.72 ± 0.05 | 1.11 ± 0.05 | 0.63 ± 0.08 |
| Spleen | 0.35 ± 0.24 | 0.24 ± 0.04 | 0.42 ± 0.06 | 0.31 ± 0.05 | 0.31 ± 0.21 |
| Brain | 0.04 ± 0.03 | 0.02 ± 0.00 | 0.05 ± 0.01 | 0.04 ± 0.01 | 0.05 ± 0.01 |
| Intestines | 1.84 ± 0.57 | 1.38 ± 0.54 | 0.46 ± 0.04 | 1.95 ± 1.24 | 0.35 ± 0.08 |
| Stomach | 0.63 ± 0.69 | 0.32 ± 0.06 | 0.27 ± 0.11 | 0.45 ± 0.07 | 0.34 ± 0.29 |
| Pancreas | 0.25 ± 0.22 | 0.18 ± 0.08 | 0.21 ± 0.06 | 0.25 ± 0.05 | 0.18 ± 0.11 |
| Tumor/Blood | 1.41 ± 0.32 | 1.25 ± 0.21 | 0.99 ± 0.24 | 0.61 ± 0.02 | 0.54 ± 0.12 |
| Tumor/Muscle | 5.24 ± 1.35 | 5.64 ± 0.98 | 4.07 ± 1.13 | 3.03 ± 0.20 | 2.21 ± 0.34 |

Data are expressed as the percentage administered activity (injected dose) per gram of tissue (% ID/g) after intravenous injection of 740 kBq (20 μCi) of $^{64}$Cu-Z-FK(DOTA)-AOMK at 0.5, 2, and 24 h pi (n=3). Significant lower tumor uptake and tumor/blood, tumor/muscle ratio in MDA-MB-435 breast cancer (P<0.05) were observed.

Example 6

Protease Specificity of Probes

The above-referenced Kato et al. *Nature Chem. Biol.* 1(1): 33 (2005) describes determination of specificity of probes to various members of the cysteine protease families. This family includes caspases, legumains, gingipains and cathepsins. It was shown there that Z-FR-AOMK inhibits cathepsin B but not Cathepsin Z, H, J, C or H. The present probes may be targeted to specific cysteine proteases as taught herein and there.

We attached the chelator and radionuclide to the probe at the $P_1$ lysine side-chain. By attaching the radiolabel to a side chain, it is less likely to interfere with the binding of the AOMK warhead to the active protease. Previous work has shown that the majority of critical substrate interactions take place in the $P_2$ position of the papain family proteases. When we performed kinetic inhibition studies for the two papain family proteases cathepsins B and L we found that modification of the $P_1$ lysine of the free amine intermediate of GB111 (NH2-GB11) resulted in a 100-fold loss of potency towards cathepsin L and 30 fold loss of potency for cathepsin B.

In designing variants of the exemplified structures, one should carry out a determination of kinetic rate constants of inhibition The kinetics of inhibition may be determined by progress curve method under pseudo-first order conditions with at least 10-fold molar excess of inhibitor. Recorded progress curves are analysed by non-linear regression according to the following equation (Bieth, J. G. Theoretical and practical aspects of proteinase inhibition kinetics. *Methods Enzymol,* 248, 59-84 (1995).)

$$[P] = v_z(1 - e^{-k \cdot t})/k$$

where [P] is the product, vz is the velocity at time zero and k is the pseudo first order rate constant. Apparent rate constant (kapp) was determined from the slope of plot k versus [I]. Due to irreversible and competitive mechanism of inhibition, kapp was converted to the association constant (kass) using the equation below:

$$k_{ass} = k_{app}(1 + [S]/K_M)$$

Activity of human cathepsin L is measured using the fluorogenic substrate Z-FRAMC37 (Bachem, USA) (Km=7.1 μM) and cathepsin B is assayed against the fluorogenic substrate Z-RR-AMC38 (Bachem, USA) (Km=114 μM). Concentration of substrates during the measurement was 10 μM. Cathepsins B and L (1 nM final concentrations) were incubated with inhibitor concentrations, ranging from 10 to 2000 nM, in the presence of 10 μM of appropriate substrate. Total volume during the measurement is 100 μl. Increase of fluorescence (370 nm excitation, 460 nm emission) is continuously monitored for 30 minutes by Spectramax M5 spectrofluorimeter. (Molecular Devices, USA) and inhibition curves were recorded. DMSO concentration during all measurements was 3.5%.

Example 7

Figure 5:
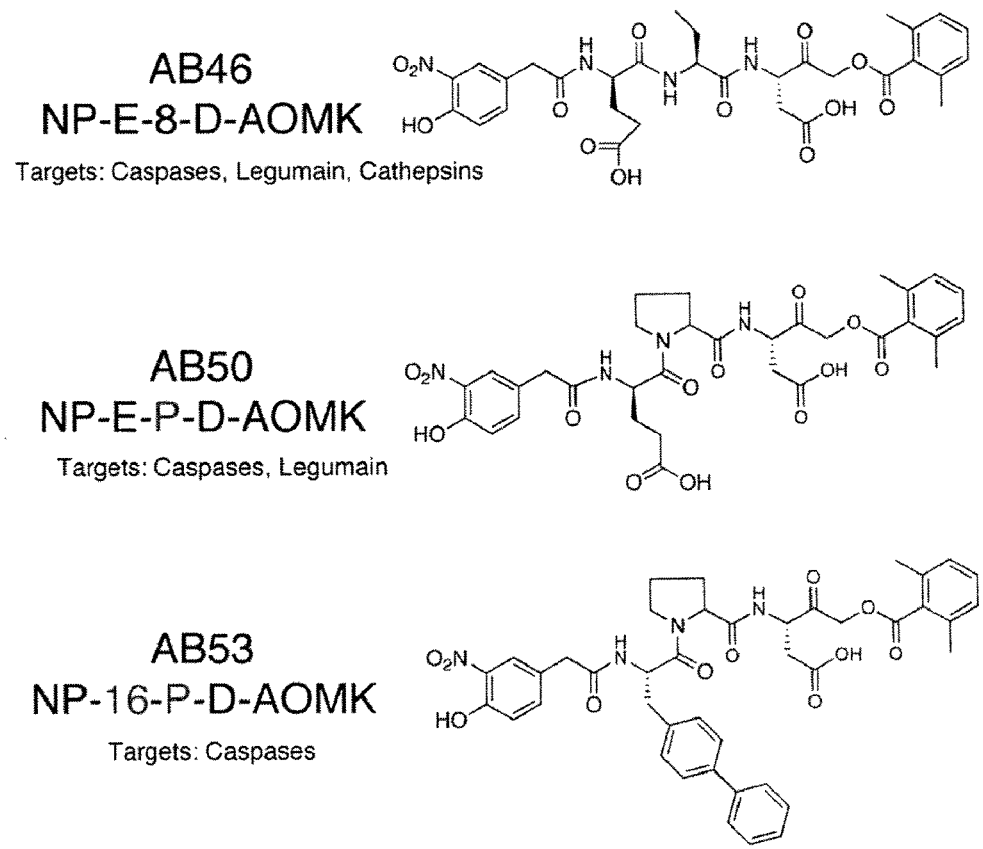
FIG. 5 shows structural representations of AOMK peptide probes having $P_1$-$P_3$ and an $R_1$ group containing a nitro group (O2N—) for radiolabeling.

Studies with R1 Labeled Radiolabeled Probe Having $P_1 = D$, $P_2 = P$, $P_3 = 16$ Referring now to FIG. 5, structure of a caspase probe (as opposed to a cathepsin probe) (AB53) is shown. The figure illustrates how modifications to $P_1$ through $P_3$ were made and how the target specificity of the probe changed as a result. The positions of $P_3$, $P_2$ and $P_1$ (in that order) are represented by E-8-D, E-P-D and 16-P-D, where 16 is an artificial amino acid side chain as shown in FIG. 4.

Distribution studies were done in mice that were treated with dexamethazone (IP injection) to induce apoptosis in the thymus. This animal model is further described, e.g., in Casteels et al. "Sex Difference in Resistance to Dexamethasone-Induced Apoptosis in NOD Mice," *Diabetes,* 47:1033-1037, 1998. AB53 was labeled with $^{125}$I at the nitrophenol capping group.

Figure 6:
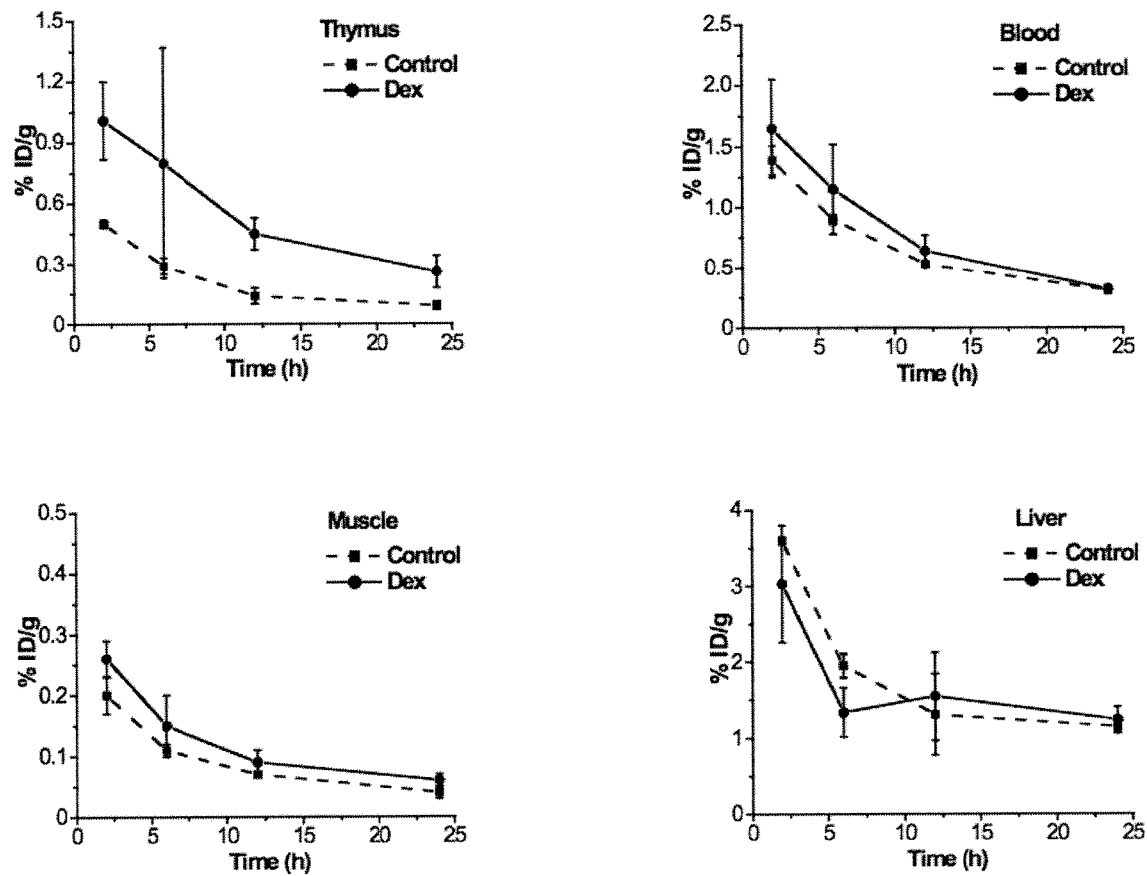
FIG. 6 shows graphically the uptake of a $^{125}$I-labeled caspase specific compound, AB53, shown in FIG. 5 in a dexamethasone apoptosis animal model. This probe accumulates specifically in the thymus tissue that is undergoing apoptosis and not in other tissues or blood. Graphs are for thymus, blood, muscle and liver.

Referring now to FIG. 6, data for the uptake of the probe in different tissues was obtained. Presented there are four graphs, one for thymus (FIG. 6A), one for blood (FIG. 6B) one for muscle (FIG. 6C) and one for liver (FIG. 6D), showing data from the in vivo uptake studies with $^{125}$I-AB53. Graphs plot radioactivity as percent of initial dose/g of tissue from $^{125}$I measured in different organs over time. One can observe the increased uptake of the probe in the dexamethasone treated thymus (FIG. 6A). This shows that the probe level is increasing in the thymus, where apoptosis is increasing. This differential uptake is not observed in other tissues.

Example 8

In Vivo Imaging with Cathepsin Binding Probes

In this example, a probe binding to cathepsin, rather than caspase was evaluated. The target enzyme was altered, as described above, by modifying $P_1$, $P_2$ and $P_3$ positions. The exemplified probe has the residues ($P_3$-$P_1$) Phe, Phe and Lys. It has a general structure as follows:

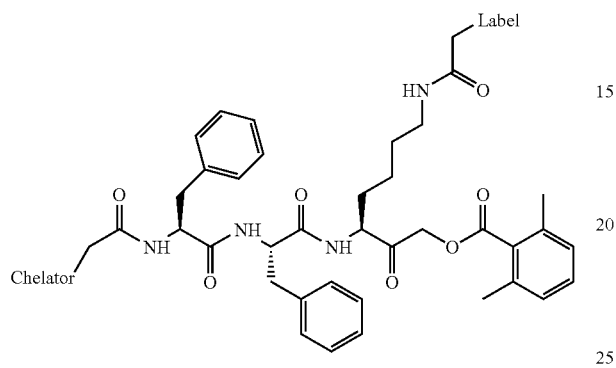

A label is linked through the Lys and a chelator is linked to the end Phe. The following specific compounds were prepared:

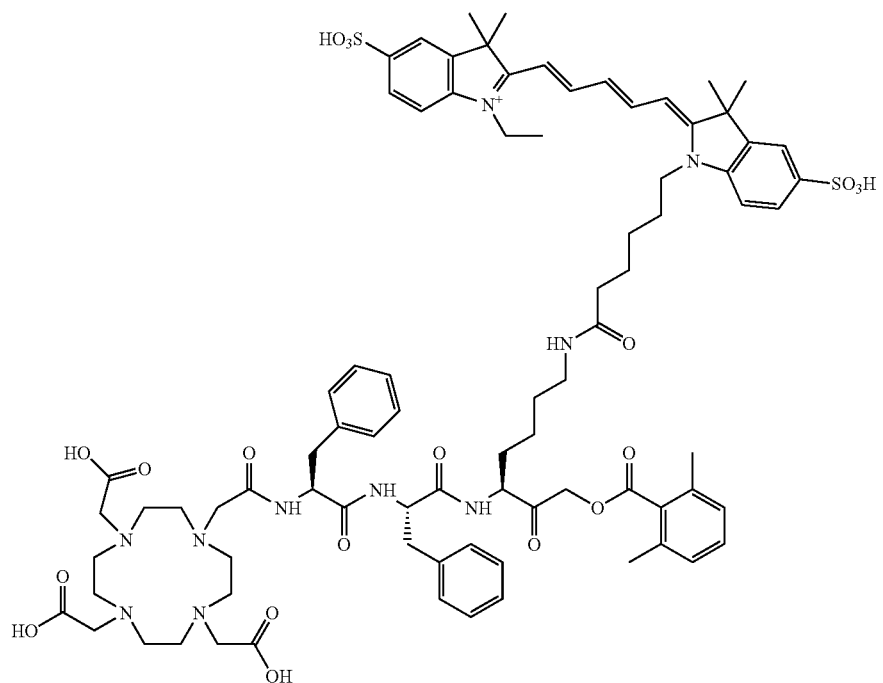

DOTA-FFK(Cy$_5$)-AOMK (GB170)

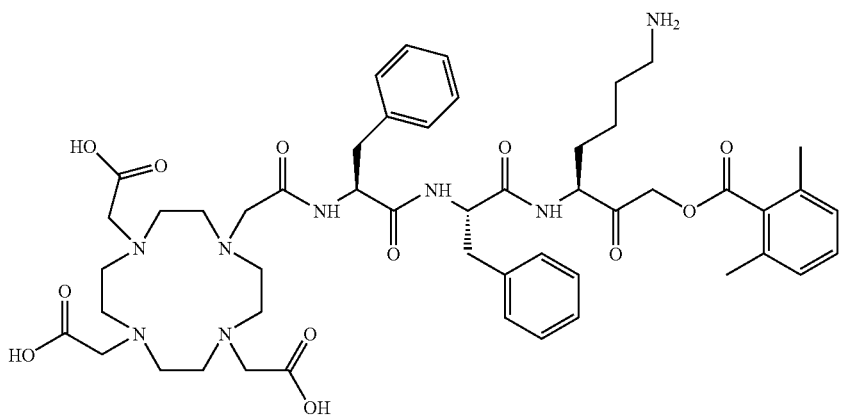 [SMILES: Cc1cccc(C)c1C(=O)OCC(=O)[C@H](CCCCN)NC(=O)[C@H](Cc1ccccc1)NC(=O)[C@H](Cc1ccccc1)NC(=O)CN1CCN(CC(=O)O)CCN(CC(=O)O)CCN(CC(=O)O)CC1]

DOTA-FFK-AOMK (GB172), and

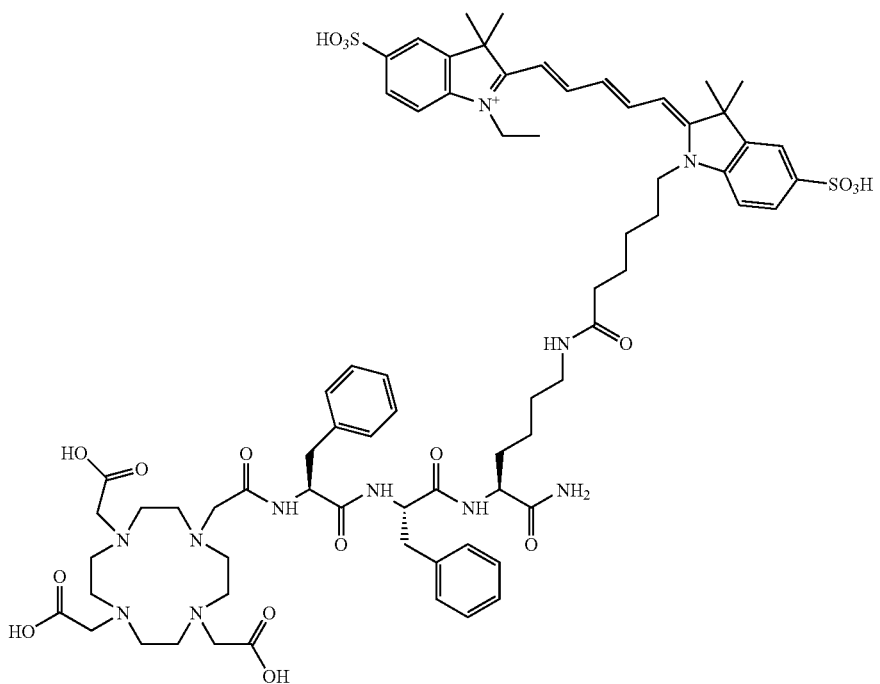 [SMILES: CC[N+]1=C(/C=C/C=C/C=C2\N(CCCCCC(=O)NCCCC[C@H](NC(=O)[C@H](Cc3ccccc3)NC(=O)[C@H](Cc3ccccc3)NC(=O)CN3CCN(CC(=O)O)CCN(CC(=O)O)CCN(CC(=O)O)CC3)C(N)=O)c3ccc(S(=O)(=O)O)cc3C2(C)C)C(C)(C)c2cc(SOOO)ccc21]

DOTA-FFK(Cy$_5$)-AOMK-Amide (GB173)

As can be seen, the structures are varied by the addition of a Cy5 label or the omission of the AOMK warhead (DOTA-FFK(Cy5)-AOMK. These compounds may be synthesized as described above and, as to the peptidyl-AOMK portion, as described in Blum et al., "Dynamic Imaging of protease activity with fluorescently quenched activity-based probes," *Nature Chem. Biol.* 1(4) 203-209 (2005). These compounds were tested in a tumor xenograft model previously described in connection with our work with fluorescent probes. See, copending Ser. No. 11/502,255, published as US 2007-0036725-A1.

Essentially, two to four weeks prior to imaging MDA-MB 231 or C2C12/ras cells (a myoblast cell line wherein ras blocks differentiation) at $2\times10^6$ cell per spot were injected subcutaneous to the back of Balb-c nude mice.

Mice bearing tumors of similar size were injected intravenous via the tail vein with a DMSO/PBS solution of the compound to be tested. DMSO/PBS was locally injected directly into tumors in indicated mice, 15 minutes prior to probe injection. Fluorescent intensity as photons per second per centimeter square per steradian (p/s/cm2/sr) was recorded from living mice. Images were taken at various time points after probe injection using an IVIS 200 imaging system equipped with a Cy5.5 filter. Other protocols are known and may be adapted for administration and imaging in vivo using the present compounds. Another protocol for mouse studies is given in Joyce et al. "Cathepsin cysteine proteases are effectors of invasive growth and angiogenesis during multistage tumorigenesis," *Cancer Cell* 5:443-452 (May 2004), at page 452.

Figure 7:
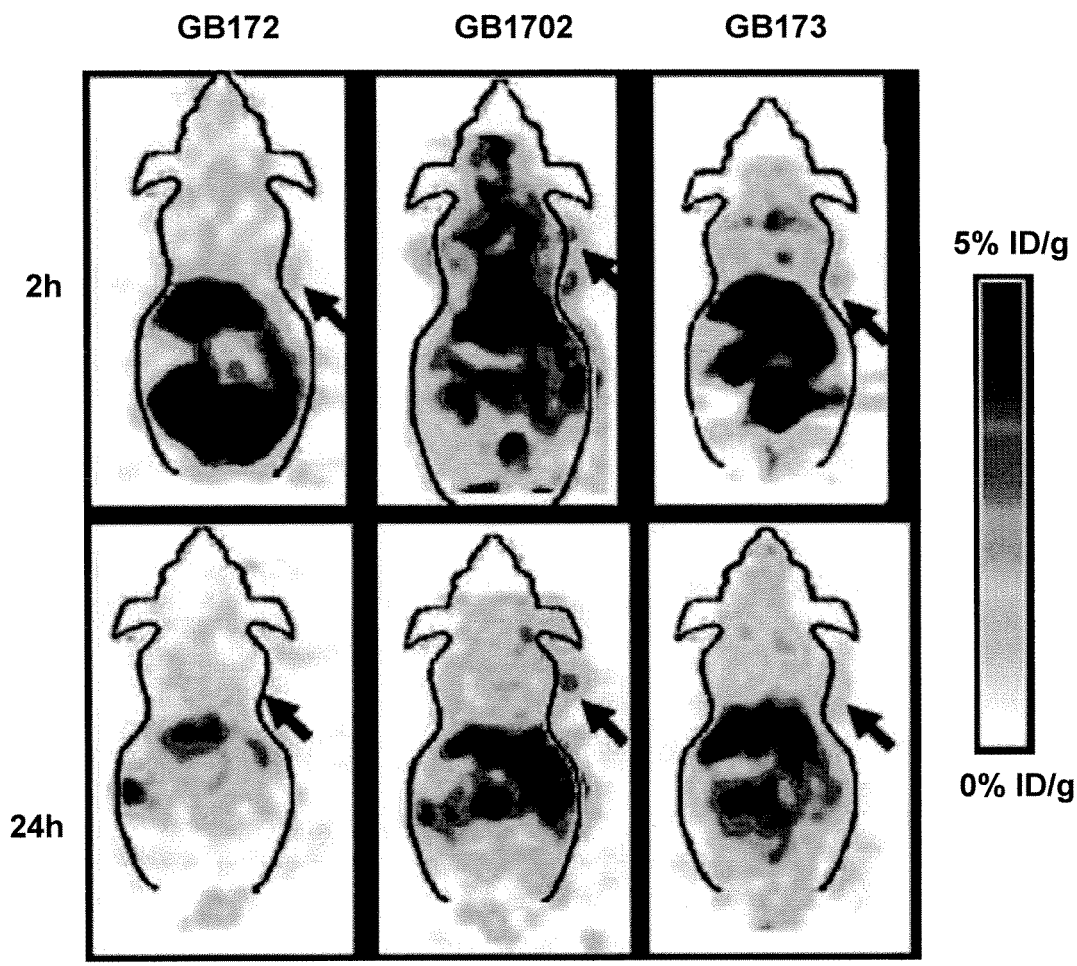
FIG. 7 shows photographically tumor uptake in mice treated with three different compounds, as indicated, and at two different times, as indicated. Mice bearing tumors derived from human C2/C12 Ras transformed cells were IV injected with $^{64}$Cu-labeled probes. Images and total probe accumulation in tumors (arrows) is shown. For purposes of reproduction, the image is converted to black and white and reversed.

In an initial attempt to make PET compatible cathepsin probes, a Cy5 tag was replaced with a group that could be used to bind $^{64}$Cu. This was compound $^{64}$Cu-DOTA-FFK-AOMK (GB172). Initial PET studies confirmed that the radiolabeled version of the probe accumulated in tumors as observed with optical probes but the overall probe uptake was very low. Without wishing to be bound by any theory, it was reasoned that this poor accumulation in tumors was likely due to changes in the pharmacokinetic (PK) and cell permeability properties as the result of removal of the large, hydrophobic fluorophore molecule. While the improved uptake of the probe having both the macrocyclic chelator and the polyaromatic functionality (Cy5), it is thought that the combination of a bulky chelator and a substituted polyaromatic provided the probe molecule with provided a balance of mass, charge and hydrophobicity that gave the probe increased permeability through the outer lipid membranes of the cells. Following this logic, a version of GB-123 that retains the Cy5 fluorophore and also contains a site for attachment of the PET imaging tag was prepared. This was 64 Cu (GB170). This new multi-modality imaging probe shows dramatically increased uptake in tumor tissues, as shown in FIG. 7 and in the table below. The arrow in the figure shows the site of the tumor, which is clearly visible in the GB170-treated animals.

Data may be summarized as follows:

| Compound | tumor uptake after 2 hrs | after 24 hours |
|---|---|---|
| GB 172 (not having Cy5) | 0.41 ± 0.07 | 0.32 ± 0.04 |
| GB 170 (having Cy5 and DOTA) | 3.17 ± 0.05 | 1.56 ± 0.23 |
| GB 173 (having DOTA and Cy5 but no AOMK) | 1.71 ± 0.08 | 0.37 ± 0.13 |

Example 9

Caspase Probe with End Label

In this example, probes are used where the end group (12 in FIG. 2A) is replaced by the chelator (10 in FIG. 2A), the $P_1$, $P_2$ and $P_3$ residues are varied, and a hydrophilic moiety, e.g., Cy5 is also attached at the distal end (away from the AOMK warhead). The conceptual structure may be represented as follows, with $P_1$, $P_2$ and $P_3$ occupied by D, P and E, respectively:

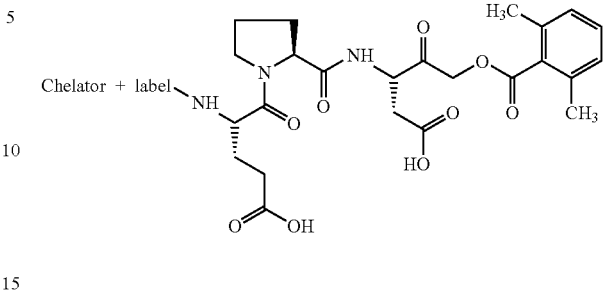

The compound is exemplified by LE5, having the following formula:

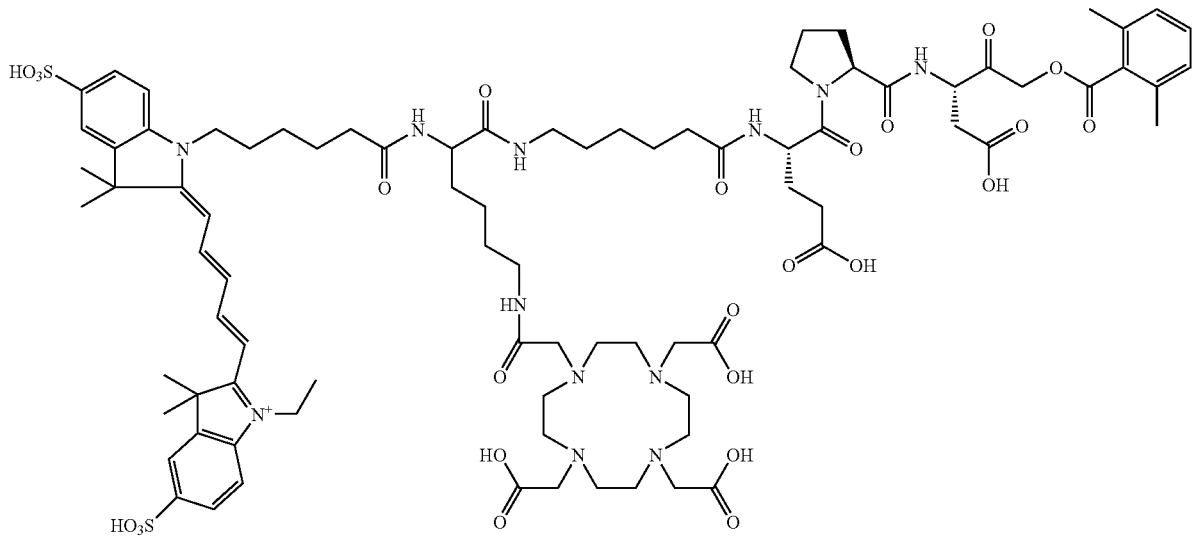 [SMILES: CC[N+]1=C(/C=C/C=C/C=C2/N(CCCCCC(=O)NC(CCCCNC(=O)CN3CCN(CC(=O)O)CCN(CC(=O)O)CCN(CC(=O)O)CC3)C(=O)NCCCCCC(=O)N[C@@H](CCC(=O)O)C(=O)N3CCC[C@H]3C(=O)N[C@@H](CC(=O)O)C(=O)COC(=O)c3c(C)cccc3C)c3ccc(SOOO)cc3C2(C)C)C(C)(C)c2cc(SOOO)ccc21]

It can be seen that the DOTA chelator and the hydrophilic Cy5 label are conjugated through a branched linker, which is attached to the distal end of the probe. The probe itself is capped with an aryl group, and consists only of the AOMK warhead and the substrate recognition quasi peptidyl chain. GB170 may be represented as DOTA-P3-P2-P1 (-label)-AOMK, where the label is attached to the P1 residue. LE5 may be represented as Label-DOTA-P3-P2-P1-AOMK, where the chelator and a polyaromatic compound (in this case a cyanine dye) are both attached to the end of the molecule distal to the AOMK warhead. The "label" does not need to function as a label.

Figure 8:
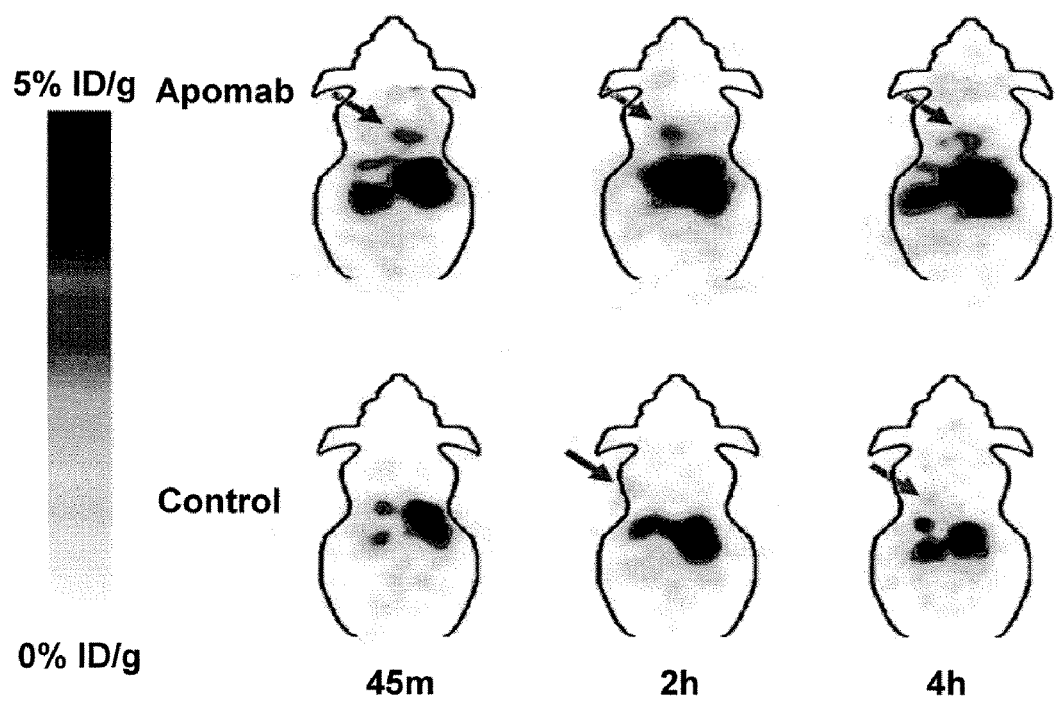
FIG. 8 shows photographically tumor uptake in vivo, where apoptosis was induced by a monoclonal antibody, APOMab, in a nude mouse bearing a colorectal tumor at the site of the arrow. For purposes of reproduction, the image is converted to black and white and reversed.

Compound LE5 was coupled (through the DOTA) with $^{64}Cu$ and tested in a tumor bearing mouse model. The colorectal tumor was formed with Colo205 cells (ATCC CCL 222). The results are shown in FIG. 8, which shows microPET images of COLO205 tumor-bearing nude mice treated for 11 hours with the apoptosis-inducing agent Apomab (10 mg/kg) or vehicle control, followed by injection of 35 μCu of $^{64}Cu$ labeled LE5. MicroPET scans were taken 45 m, 2 h, and 4 h after injection. Tumors are indicated by arrows. It can be seen that the LE5 was taken up much more significantly by the tumor after apoptosis was induced. Further details on the use and activity of this model may be found in Al-Ejeh et al., "APOMAB®, a La-Specific Monoclonal Antibody, Detects the Apoptotic Tumor Response to Life-Prolonging and DNA-Damaging Chemotherapy," PLoS ONE. 2009; 4(2): e4558. The COL0205 in an ApoMab model is further described in Chuntharapai et al., "Isotype-Dependent Inhibition of Tumor Growth In Vivo by Monoclonal Antibodies to Death Receptor 4," *The Journal of Immunology*, 2001, 166: 4891-4898.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A composition useful for in vivo imaging of tissue containing an active cysteine protease, said composition comprising a compound according to the formula:

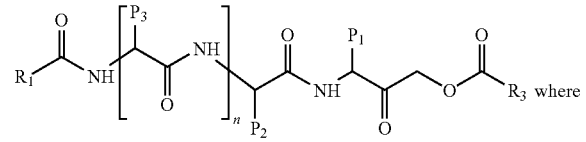

Formula I n is an integer between 0 and 2, $P_3$ being absent when n=0, and there being a $P_4$ when n=2;

$R_1$ and $R_3$ are independently selected from the group consisting of H, $NH_2$, aminocarbonyl, aryl, substituted aryl, amino, lower alkyl, or cycloalkyl;

$P_1$, $P_2$, $P_3$ and $P_4$ are independently an amino acid side chain selected from naturally occurring amino acid side chains and non-natural amino acid side chains 3, 6, 8, 23, 29, 31, 34 and 38, wherein:

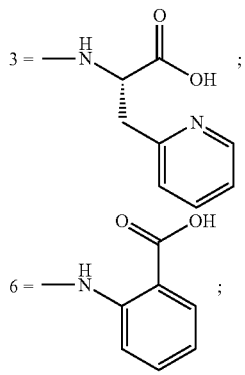

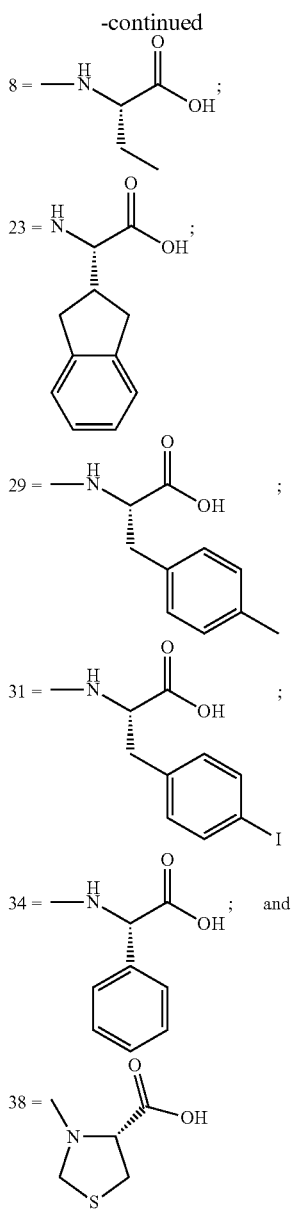

where $P_1$, if not further bonded to a chelator or a radiolabel, is optionally bonded to a cyanine dye; and one of $R_1$, $R_3$, $P_1$, $P_2$, $P_3$ or $P_4$ is further bonded to a chelator or directly to a radiolabel, which compound specifically binds a predetermined active cysteine protease.

2. The composition of claim 1 where $R_1$ and $R_3$ of Formula I are each an optionally substituted benzyl or phenyl.

3. The composition of claim 1 where one of $R_1$ or $P_1$ further comprises said chelator.

4. The composition of claim 3 where the chelator of Formula I is on $P_1$, and where $P_1$ contains a linker of 2-5 carbon atoms.

5. The composition of claim 1 where a chelator is linked by an amide linkage to a lower alkyl group in $P_1$, $P_2$, $P_3$ or $P_4$ of Formula I.

6. The composition of claim 4 where the chelator is selected from the group consisting of:
diethylenetriaminepentaacetic acid (DTPA), ethylenediaminetetraacetic acid (EDTA), 1,4,7,10-tetraazacyclododecane-N,N',N'',N'''-tetraacetate (DOTA), tetraazacyclotetradecane-N,N',N'',N'''-tetraacetic acid (TETA), hydroxyethylidene diphosphonate (HEDP), dimercaptosuccinic acid (DMSA), diethylenetriamine-tetramethylenephosphonic acid (DTTP) and 1-(p-aminobenzyl)-DTPA, 1,6-diamino hexane-N,N,N',N'-tetraacetic acid, DPDP, and ethylenebis (oxyethylenenitrilo)-tetraacetic acid.

7. The composition of claim 1 further comprising a radiolabel which is a positron emitter.

8. The composition of claim 6 where the radiolabel is selected from the group consisting of $^{131}$I, $^{99m}$Tc, $^{111}$In, $^{18}$F, $^{64}$Cu, $^{76}$Br, $^{86}$Y, $^{55}$Co, $^{124}$I and $^{125}$I.

9. The composition of claim 1 where $P_1$ of Formula I is Asp or Arg.

10. The composition of claim 1 where $P_2$ of Formula I is Pro.

11. The composition of claim 1 where $P_3$ of Formula I is aryl.

12. The composition of claim 1 where $P_2$, $P_3$ and $P_4$ of Formula I are, respectively, Arg, Phe and none.

13. The composition of claim 12 where $R_1$ and $R_3$ of Formula I are aryl.

14. The composition of claim 1 where the compound is selective for human cathepsin and does not substantially bind to any other cysteine proteases.

15. The composition of claim 1 where in Formula I $R_1$ is benzyl, n is 0, $P_2$ is tyrosine, $P_1$ is lower alkyl aminocarbonyl DOTA, and $R_3$ is dimethyl phenyl.

16. A kit for the preparation of the composition of claim 1, comprising a compound according to Formula I, and a radioisotope.

17. The kit of claim 16 wherein the radioisotope is a positron emitter.

18. A method of diagnosis of tumor activity in a mammalian body, comprising administration of a compound according to the formula:

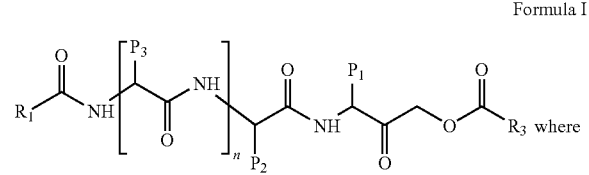

Formula I where
n is an integer between 0 and 2, $P_3$ being absent when n=0, and there being a $P_4$ when n=2;

$R_1$ and $R_3$ are independently selected from the groups consisting of H, $NH_2$, aminocarbonyl, aryl, substituted aryl, amino, lower alkyl, or cycloalkyl;

$P_1$, $P_2$, $P_3$ and $P_4$ are independently amino acid side chains selected from naturally occurring amino acid side chains and nonnatural amino acid side chains 3, 6 8, 23, 29, 31, 34 and 38 as defined in claim 1; and one of $R_1$, $R_3$, $P_1$, $P_2$, $P_3$ or $P_4$ further is bonded to a chelator or directly to a radiolabel, which compound of Formula I specifically binds to cathepsins B and L, and wherein an area having a more active tumor shows higher amount of active enzyme.

19. A method of imaging an active cysteine protease in a subject, comprising the steps of:
(a) obtaining a compound according to Formula I

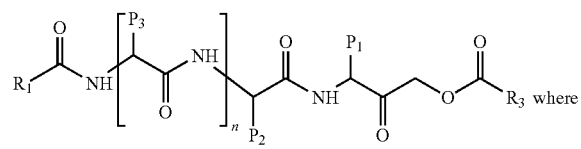

Formula I where
n is an integer between 0 and 2, $P_3$ being absent when n=0, and there being a $P_4$ when n=2;

$R_1$ and $R_3$ are independently selected from the group consisting of H, $NH_2$, aminocarbonyl, aryl, substituted aryl, amino, lower alkyl, or cycloalkyl;

$P_1$, $P_2$, $P_3$ and $P_4$ are independently an amino acid side chain selected from naturally occurring amino acid side chains and non-natural amino acid side chains 3, 6, 8, 23, 29, 31, 34 and 38, wherein:

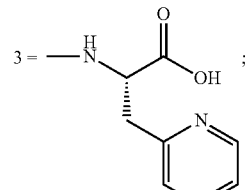

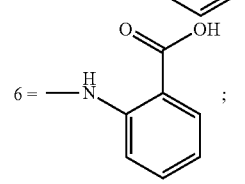

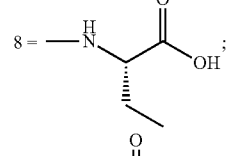

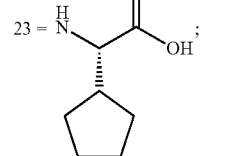

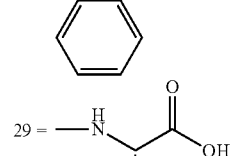

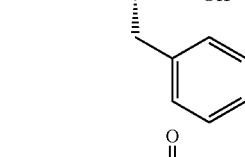

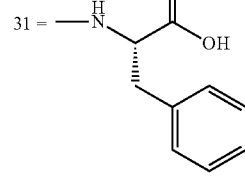

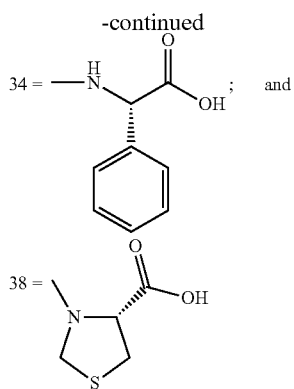

where P$_1$, if not further bonded to a chelator or a radiolabel, is optionally bonded to a cyanine dye; and one of R$_1$, R$_3$, P$_1$, P$_2$, P$_3$ or P$_4$ is bonded to a chelator and a radiolabel or directly to a radiolabel;

(b) intravenously administering to the subject a composition comprising a compound of step (a); and (c) obtaining an image of the administered compound in step (b) after a time sufficient to allow the compound to bind to and be cleaved by an active cysteine protease selected from the group consisting of cathepsin B, cathepsin L, caspase 3, caspase 7, caspase 8, and caspase 9, wherein the imaging is done by detecting gamma radiation or positron emission and portions of the subject which have higher levels of said active cysteine protease are distinguished from other portions.

20. A method of imaging an active cysteine pprotease in a subject, comprising the steps of:

(a) obtaining a compound according to Formula I of claim 1, wherein said Formula is defined to include a radiolabel;

(b) intravenously administering to the subject a composition comprising a compound of step (a); and (c) obtaining an image of the administered compound in step (b) after a time sufficient to allow the compound to bind to and be cleaved by an active cysteine protease selected from the group consisting of cathepsin B, cathepsin L, caspase 3, caspase 7, caspase 8, and caspase 9, wherein the imaging is done by detecting gamma radiation or positron emission and portions of the subject which have higher levels of said active cysteine protease are distinguished from other portions.

21. The method of claim 19 where P$_2$ is aryl.

22. The method of claim 19 where P$_2$, R$_1$ and R$_3$ are aryl.

23. The method of claim 19 where the radiolabel is on P$_1$ or R$_1$.

24. The method of claim 19 further comprising the step of reacting a macrocyclic chelator with a sulfonosuccimimide in order to couple it to the compound.

25. The method of claim 19 further comprising the step of heating the compound in the presence of a radioactive metal to bind the radioactive metal to a DOTA macrocyclic chelator.

26. The composition of claim 1 wherein P1 is linked to a Cy5 label.

27. The composition of claim 26 wherein formula I has the following structure:

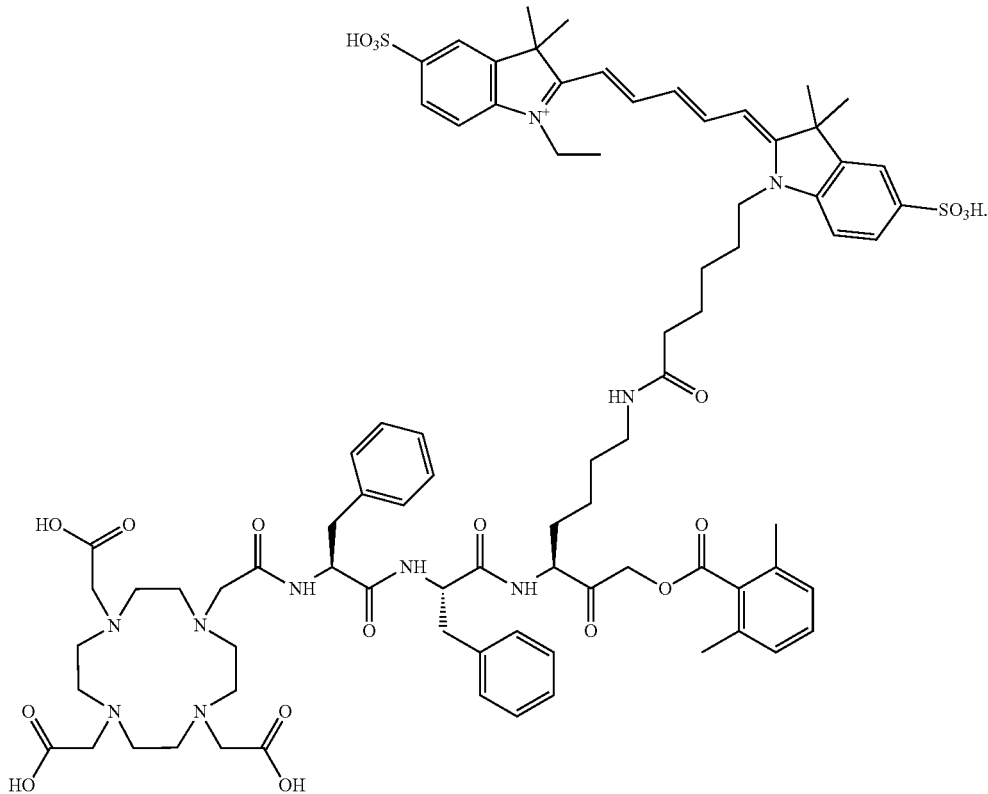 [SMILES: CC[N+]1=C(/C=C/C=C/C=C2\N(CCCCCC(=O)NCCCC[C@H](NC(=O)[C@H](Cc3ccccc3)NC(=O)[C@H](Cc3ccccc3)NC(=O)CN3CCN(CC(=O)O)CCN(CC(=O)O)CCN(CC(=O)O)CC3)C(=O)COC(=O)c3c(C)cccc3C)c3ccc(S(=O)(=O)O)cc3C2(C)C)C(C)(C)c2cc(S(=O)(=O)O)ccc21]

28. The composition of claim 1 where the substituted aryl is selected from the group consisting of:

2-nitro, 3-hydroxy, methyl and dimethyl substituted benzyl and benzyloxycarbonyl.

29. The method of claim 18 where the substituted aryl is selected from the group consisting of:

2-nitro, 3-hydroxy, methyl and dimethyl substituted benzyl and benzyloxycarbonyl.

* * * * *